US007620454B2

(12) United States Patent
Dinsmoor et al.

(10) Patent No.: US 7,620,454 B2
(45) Date of Patent: Nov. 17, 2009

(54) GASTRO-ELECTRIC STIMULATION FOR REDUCING THE ACIDITY OF GASTRIC SECRETIONS OR REDUCING THE AMOUNTS THEREOF

(75) Inventors: David A. Dinsmoor, Minneapolis, MN (US); Warren L. Starkebaum, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 131 days.

(21) Appl. No.: 10/441,785

(22) Filed: May 19, 2003

(65) Prior Publication Data
US 2004/0236381 A1 Nov. 25, 2004

(51) Int. Cl.
*A61N 1/18* (2006.01)

(52) U.S. Cl. .......................... 607/40; 607/41; 607/129; 607/130; 607/131; 607/133; 600/361; 604/891.1

(58) Field of Classification Search ............. 607/40–41, 607/133, 129–131; 604/891.1; 600/361
See application file for complete search history.

(56) References Cited

U.S. PATENT DOCUMENTS

| 3,719,183 | A | | 3/1973 | Schwartz |
| 3,902,501 | A | | 9/1975 | Citron et al. |
| 4,106,512 | A | | 8/1978 | Bisping |
| 4,279,886 | A | | 7/1981 | Allen |
| 4,476,868 | A | | 10/1984 | Thompson |
| 4,566,063 | A | | 1/1986 | Zolnowsky et al. |
| 4,844,076 | A | | 7/1989 | Lesho et al. |
| 4,979,511 | A | | 12/1990 | Terry, Jr. |
| 5,170,801 | A | | 12/1992 | Casper et al. |
| 5,188,104 | A | * | 2/1993 | Wernicke et al. ............ 607/40 |
| 5,193,539 | A | | 3/1993 | Schulman et al. |
| 5,193,540 | A | | 3/1993 | Schulman et al. |

(Continued)

FOREIGN PATENT DOCUMENTS

WO    WO8803389    5/1988

(Continued)

OTHER PUBLICATIONS

Calvin A. Richins, 'The Innervation of the Pancreas', St. Louis University School of Medicine, Missouri, pp. 223-236.

(Continued)

*Primary Examiner*—Carl H Layno
*Assistant Examiner*—Deborah Malamud
(74) *Attorney, Agent, or Firm*—Shumaker & Sieffert, P.A.

(57) ABSTRACT

A gastro-electric stimulation system includes an INS for producing an electrical stimulation signal, at least one medical electrical lead, and at least two electrical contacts. The medical electrical lead has a proximal end and a distal end, the proximal end being connected to the INS, the distal end being adapted for placement in or near a patient's stomach or appropriate nerve or nerve portion. The electrodes are disposed near the distal end of the medical electrical lead, and are electrically connected through the medical electrical lead to the INS to receive the electrical stimulation signal and convey such signal to the selected electrode implant position. The electrical stimulation signal is provided in an amount and manner adapted to increase the pH of the gastric acid in the patient's stomach and/or to decrease the amount of gastric acid produced thereby.

33 Claims, 24 Drawing Sheets

U.S. PATENT DOCUMENTS

| | | | |
|---|---|---|---|
| 5,199,428 | A | 4/1993 | Obel et al. |
| 5,207,218 | A | 5/1993 | Carpentier et al. |
| 5,231,988 | A | 8/1993 | Wernicke et al. |
| 5,263,480 | A | 11/1993 | Wernicke et al. |
| 5,279,607 | A | 1/1994 | Schentag et al. |
| 5,292,344 | A * | 3/1994 | Douglas ............. 607/40 |
| 5,300,107 | A | 4/1994 | Stokes et al. |
| 5,324,316 | A | 6/1994 | Schulman et al. |
| 5,330,507 | A | 7/1994 | Schwartz |
| 5,358,514 | A | 10/1994 | Schulman et al. |
| 5,395,366 | A | 3/1995 | D'Andrea et al. |
| 5,405,367 | A | 4/1995 | Schulman et al. |
| 5,423,872 | A | 6/1995 | Cigaina |
| 5,425,751 | A | 6/1995 | Baeten et al. |
| 5,501,703 | A | 3/1996 | Holsheimer et al. |
| 5,540,730 | A | 7/1996 | Terry |
| 5,640,764 | A | 6/1997 | Strojnik |
| 5,643,330 | A | 7/1997 | Holsheimer et al. |
| 5,660,163 | A | 8/1997 | Schulman et al. |
| 5,690,691 | A * | 11/1997 | Chen et al. ............. 607/40 |
| 5,699,793 | A | 12/1997 | Brasile |
| 5,716,385 | A | 2/1998 | Mittal |
| 5,750,926 | A | 5/1998 | Schulman et al. |
| 5,791,344 | A | 8/1998 | Schulman et al. |
| 5,800,465 | A | 9/1998 | Thompson et al. |
| 5,836,994 | A * | 11/1998 | Bourgeois ............. 607/40 |
| 5,861,014 | A | 1/1999 | Familioni |
| 5,876,425 | A | 3/1999 | Gord et al. |
| 5,916,239 | A | 6/1999 | Geddes et al. |
| 5,917,346 | A | 6/1999 | Gord |
| 5,919,216 | A | 7/1999 | Houben et al. |
| 5,925,070 | A | 7/1999 | King et al. |
| 5,941,906 | A | 8/1999 | Barreras et al. |
| 5,957,958 | A | 9/1999 | Schulman et al. |
| 5,999,848 | A | 12/1999 | Gord et al. |
| 6,043,437 | A | 3/2000 | Schulman et al. |
| 6,051,017 | A | 4/2000 | Loeb et al. |
| 6,067,474 | A | 5/2000 | Schulman et al. |
| 6,083,249 | A | 7/2000 | Familoni |
| 6,088,608 | A | 7/2000 | Schulman et al. |
| 6,091,992 | A * | 7/2000 | Bourgeois et al. ............. 607/40 |
| 6,097,984 | A * | 8/2000 | Douglas ............. 607/40 |
| 6,098,629 | A | 8/2000 | Johnson et al. |
| 6,178,349 | B1 | 1/2001 | Kieval |
| 6,185,452 | B1 | 2/2001 | Schulman et al. |
| 6,205,361 | B1 | 3/2001 | Kuzma et al. |
| 6,208,894 | B1 | 3/2001 | Schulman et al. |
| 6,212,431 | B1 | 4/2001 | Hahn et al. |
| 6,214,032 | B1 | 4/2001 | Loeb et al. |
| 6,238,423 | B1 * | 5/2001 | Bardy ............. 607/40 |
| 6,243,607 | B1 * | 6/2001 | Mintchev et al. ............. 607/40 |
| 6,259,937 | B1 | 7/2001 | Schulman et al. |
| 6,285,897 | B1 | 9/2001 | Kilcoyne et al. |
| 6,315,721 | B2 | 11/2001 | Schulman et al. |
| 6,363,937 | B1 * | 4/2002 | Hovda et al. ............. 128/898 |
| 6,381,496 | B1 | 4/2002 | Meadows et al. |
| 6,388,345 | B1 | 5/2002 | Stimpson |
| 6,393,325 | B1 | 5/2002 | Mann et al. |
| 6,401,718 | B1 | 6/2002 | Johnson et al. |
| 6,421,566 | B1 | 7/2002 | Holsheimer |
| 6,428,469 | B1 | 8/2002 | Iddan et al. |
| 6,449,511 | B1 * | 9/2002 | Mintchev et al. ............. 607/40 |
| 6,453,199 | B1 * | 9/2002 | Kobozev ............. 607/40 |
| 6,516,227 | B1 | 2/2003 | Meadows et al. |
| 6,535,764 | B2 * | 3/2003 | Imran et al. ............. 607/40 |
| 6,591,137 | B1 * | 7/2003 | Fischell et al. ............. 607/40 |
| 6,612,983 | B1 | 9/2003 | Marchal |
| 6,754,536 | B2 * | 6/2004 | Swoyer et al. ............. 607/40 |
| 6,832,114 | B1 | 12/2004 | Whitehurst et al. |
| 6,853,862 | B1 | 2/2005 | Marchal et al. |
| 6,895,278 | B1 * | 5/2005 | Gordon ............. 607/40 |
| 6,971,393 | B1 | 12/2005 | Mamo et al. |
| 6,999,819 | B2 | 2/2006 | Swoyer et al. |
| 7,167,751 | B1 | 1/2007 | Whitehurst et al. |
| 2002/0055734 | A1 | 5/2002 | Houzego et al. |
| 2002/0082665 | A1 | 6/2002 | Haller et al. |
| 2002/0103424 | A1 | 8/2002 | Swoyer et al. |
| 2002/0116030 | A1 | 8/2002 | Rezai |
| 2002/0128694 | A1 | 9/2002 | Holsheimer |
| 2002/0132226 | A1 | 9/2002 | Nair et al. |
| 2002/0135556 | A1 | 9/2002 | Nakajima et al. |
| 2002/0165589 | A1 | 11/2002 | Imran et al. |
| 2002/0193842 | A1 | 12/2002 | Forsell |
| 2002/0198470 | A1 | 12/2002 | Imran |
| 2003/0014086 | A1 | 1/2003 | Sharma |
| 2003/0045914 | A1 | 3/2003 | Cohen et al. |
| 2004/0044376 | A1 * | 3/2004 | Flesler et al. ............. 607/40 |
| 2004/0193229 | A1 | 9/2004 | Starkebaum et al. |
| 2005/0240231 | A1 * | 10/2005 | Aldrich et al. ............. 607/3 |

FOREIGN PATENT DOCUMENTS

| | | |
|---|---|---|
| WO | WO0176690 | 10/2001 |
| WO | WO0238217 | 5/2002 |
| WO | WO02/087657 | 11/2002 |
| WO | WO02/089655 | 11/2002 |

OTHER PUBLICATIONS

'Laboratory Aids in Diagnosis of Pancreatic Disease', Section XVI-Plate 23.

Kang et al., 'Pancreatic Exocrine-Endocrine Interrelationship', Pancreas Update, vol. 28, No. 3, pp. 551-569, Sep. 1999, Gastroenterology Clinics of North America.

Holst et al., 'Nervous Control of Pancreatic Exocrine Secretion in Pigs', Acta physiol, scand. 1979. 105. pp. 33-51, Institute of Medical Physiology C. University of Copenhagen and the Department of Clinical Chemistry, Bispebjerg Hospital, Copenhagen, Denmark.

Fiorucci et al. 'Duodenal Osmolality Drives Gallbladder Emptying in Humans'. pp. 698-704. Digestive Diseases and Sciences, vol. 35, No. 6, Jun. 1990.

Chen, Jian de Z., et al., 'Serosal and Cutaneous Recordings of Gastric Myoelectrical Activity in Patients with Gastroparesis', the American Physiological Society, 1994, pp. G90-G98.

Durand, Dominique. 'Electric Stimulation of Excitable Tissue', The Biomedical Engineering Handbook. Joesph D. Bronzino (ed.). Boca Raton, FL: CRC Press, Inc. 1995. pp. 229-251.

Davison, J.M. et al. 'Plasma Osmolality and Urinary Concentration and Dilution During and After Pregnancy: Evidence that Lateral Recumbency Inhibits Maximal Urinary Concentrating Ability'. British Journal of Obstetrics and Gynaecology. May 1981, vol. 88, pp. 472-479.

Boissonade, Fiona M. et al. "Fos Expression in Ferret Dorsal Vagal Complex After Peripheral Emetic Stimuli". The American Physiological Society, 1994, pp. R1118-R1126.

Minoti V. Apte et al., Chronic Pancreatitis: "Complications and Management", 1 Clin Gastroenterol 29(3):p. 225-240 (1999).

Kenneth L. Koch et al., "Functional Disorders of the Stomach, Seminars in Gastrointestinal Disease", vol. 7, No. 4, 185-195 (Oct. 1996).

Kenneth L. Koch, "Gastroparesis Diagnosis and Management", Practical Gastroenterology (Nov. 1997).

Babjide O. Familoni et al., "Efficacy of Electrical Stimulation at Frequencies Higher than Basal Rate in-Canine Stomach", Digestive Diseases and Sciences, vol. 42, No. 5 (May 1997).

Babajide O. Familoni, "Electrical Stimulation at a Frequency Higher than Basal Rage in Human Stomach", Digestive Diseases and Sciences, vol. 42, No. 5 (May 1997).

Schwartz T.W., Pancreatic Polypeptide: A Hormone Under Vagal Control, Gastroenterology, 85(6)1411-1425 (Dec. 1983).

Koch et al, "Electrogastrography-" An Illustrated Guide to Gastrointestinal Motility $2^{nd}$ Ed. pp. 290-307, (1993).

Grundy et al., "Effects of Stimulation of the Bagus nerve in Bursts on Gastric Acid Secretion And Motility in the Anaesthestized Ferret," *J. Physiol.*, 333: pp. 451-461, 1982.

Netter, Frank, "Book-The Ciba Collection of medical Illustrations"vol. 3 Digestive System, Paret III Liver, Billary Tract and Pancrease (1964).

Sasaki, N. et al., "Selective Action of a CCK-B/gastrin receptor antagonist, S-0509, on pentagastrin-, peptone meal and beer stimulated gastric acid secretion in dogs," Aliment Pharmacol Ther., 14 479-488, 2000.

Sjodin, "Gastric Acid Responses to Graded Vagal Stimulation in the Anaesthetized Cat," *Digestion* 12: 17-24 (1975).

Hahn et al. "Stimulatory Effects of the Central Amygdaloid Nucleus on Pancreatic Exocrine Secretion in Rats" Neurosci Lett, Mar. 14, 1994: 169 (1-2) 43-6.

Physician's Manual NeuroCybernetic Prosthesis, Bipolar lead, Model 300, Sep. 2001.

"Autonomous Electrostimulator of the Gastrointestinal Tract," Institute of Medical-Ecological Problem of Vision, http://www.nmpz.org/english/aes.phtml, (1996) printed Sep. 28, 2007 (11 pgs.).

U.S. Appl. No. 10/441,786, filed May 19, 2003, "Gastro-Electric Stimulation for Increasing the Acidity of Gastric Secretions or Increasing the Amounts Thereof," by Dinsmoor et al.

Sakaguchi et al., "The Effect of Electrical Stimulation of the Hepatic Branch of the Vagus Nerve on the Secretion of Gastric Acid in the Rat," Neuroscience Letters, 13, pp. 25-28 (1979).

Zolotarev et al., "Selective Regulation of Acid, Pepsinogen, and Bicarbonate Secretion in the Stomach by Different C-Fiber Populations of Vagus Nerve," Bulletin of Experimental Biology and Medicine, vol. 133, No. 3, pp. 210-213 (2002).

Smith et al., "Control Factors in the Release of Gastrin by Direct Electrical Stimulation of the Vagus," Digestive Diseases, vol. 20, No. 1, pp. 13-22 (1975).

Sharkey et al., "Capsaicin-sensitive vagal stimulation-induced gastric acid secretion in the rat: evidence for cholinergic vagal afferents," Br. J. Pharmacol, 103, pp. 1997-2003 (1991).

Office Action dated Feb. 12, 2008 for U.S. Appl. No. 10/441,786 (19 pgs.).

AstraZeneca et al., "First Principles of Gastroenterology," Adapted from First Principles of Gastroenterology: The Basis of Disease and an Approach to Management, 2000; pp. 138-145; http://www.gastroresource.com/GITextbook/en/Default.htm.

Sobhani et al. "Vagal Stimulation Rapidly Increases Leptin Secretion in Human Stomach," Gastroenterology, 2002: 122: pp. 259-263.

Office Action dated Aug. 20, 2008 for U.S. Appl. No. 10/441,786 (20 pgs.).

Request for Continued Examination and Amendment dated Nov. 20, 2008 for U.S. Appl. No. 10/441,786 (21 pgs.).

Schubert et al., "Reviews in Basic and Clinical Gastroenterology," Gastroenterology, 134, pp. 1842-1860, May, 2008.

Berthoud et al., "Characteristics of gastric and pancreatic responses to vagal stimulation with varied frequencies: evidence for different fiber calibers?" Journal of the Autonomic Nervous System, 19, pp. 77-84, Apr. 1987.

Office Action dated Feb. 19, 2009 for U.S. Appl. No. 10/441,786 (11 pgs.).

Response dated May 19, 2009 for U.S. Appl. No. 10/441,786 (9 pgs.).

* cited by examiner

IMPLANT SYSTEM COMPONENTS

IMPLANT HARDWARE

IMPLANTABLE NEUROSTIMULATOR:
MEDTRONIC ITREL3 (MODEL 7425G)

NEUROMUSCULAR LEADS (2):
MEDTRONIC MODEL 4351

STIMULATION PARAMETERS

AMPLITUDE: 5 milliamps
PULSE WIDTH: 330 μsec
RATE: 14Hz
CYCLE ON TIME: 0.1 sec
CYCLE OFF TIME: 5.0 sec

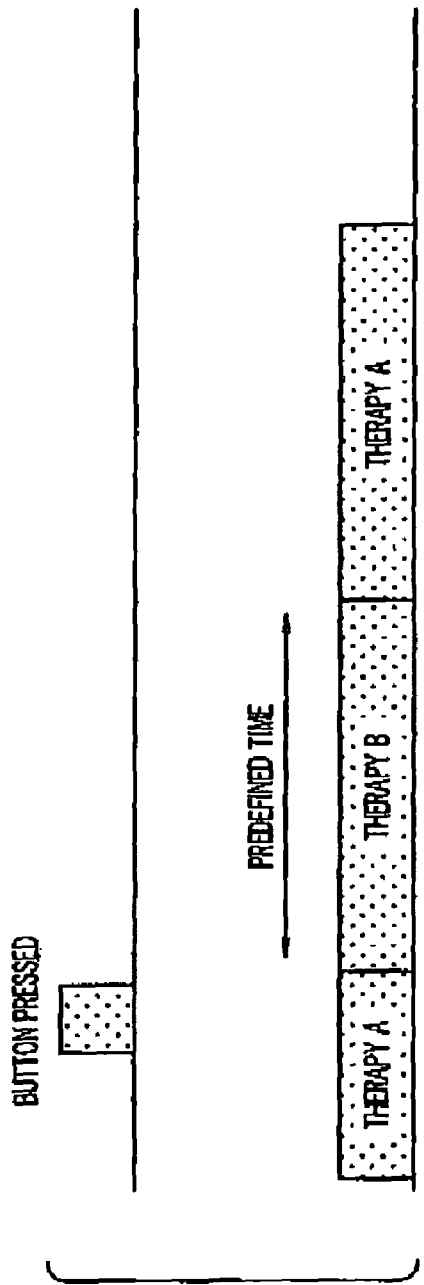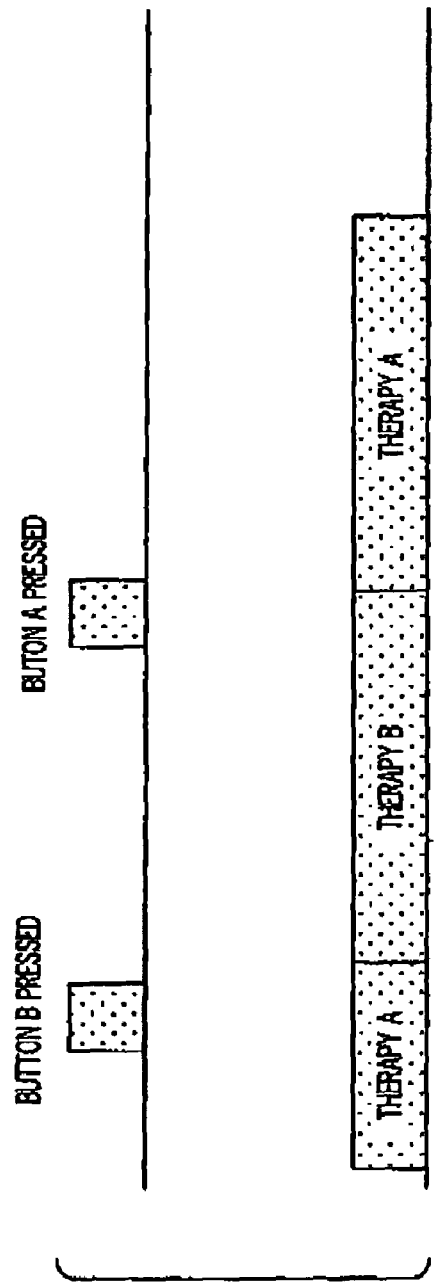

GASTRO-ELECTRIC STIMULATION FOR REDUCING THE ACIDITY OF GASTRIC SECRETIONS OR REDUCING THE AMOUNTS THEREOF

RELATED APPLICATIONS

This application hereby incorporates by reference herein in their respective entireties U.S. Patent Application Publication No. 20040236382 to Dinsmoor et al. entitled "Gastro-Electric Stimulation for Increasing the Acidity of Gastric Secretions or Increasing the Amounts Thereof" and U.S. Patent Application Publication No. 20040193229 to Starkebaum et al. entitled "Gastric Electric Stimulation for Treatment of Gastro-Esophageal Reflux Disease," both such applications being filed on even date herewith.

BACKGROUND OF THE INVENTION

The present invention relates to medical devices used to electrically stimulate the digestive system, and more specifically to devices employed to electrically stimulate portions of the digestive system and/or the vagus nerve to reduce the acidity of gastric acid secretions and/or reduce the amount of gastric acid secretions produced by the stomach.

The medical device industry produces a wide variety of electronic and mechanical devices for treating patient medical conditions. Depending upon a patient's medical condition, medical devices may be surgically implanted or connected externally to the patient. Physicians use medical devices alone or in combination with drug therapies and surgery to treat patient medical conditions. For some medical conditions, medical devices provide the best, and sometimes the only, therapy to treat a medical condition and restore an individual to a more healthful condition and a fuller life. One type of medical device applied to treat conditions receptive to neurological therapy is an implantable neurostimulator (hereafter "INS"). An INS applies an electrical signal to the nervous system to create a response such as reducing patient pain or influencing a body organ, and may also be employed to apply an electrical signal to the enteric nervous system.

The digestive system is composed of the digestive tract, accessory organs and the enteric nervous system, and functions to prepare food for absorption and use by the body. The enteric nervous system is the digestive system's nervous system, and it functions to both receive and transmit information. This system receives neurological information from the digestive system through afferent nerves, and issues instructions through efferent nerves. Gastric myoelectrical activity is described by Kenneth Koch et al. in Electrogastrography, "An Illustrated Guide To Gastrointestinal Motility," $2^{nd}$ Ed., pp. 290-307 (1993). The vagus nerve contains both afferent and efferent nerves and provides nervous system connectivity between digestive system organs, including between the stomach and brain. The gastric frequency of a patient is generally about 3.0 cycles per minute. The enteric nervous system is believed to exert some control over gastric acid secretion functions.

Previous drug-based treatments for lowering the acidity of gastric acid do not satisfactorily treat some patient conditions, and moreover may suffer from a variety of undesirable side effects, especially when used over long periods of time. Pharmaceutical products aimed at reducing gastric secretion acidity such as NEXIUM®, PREVACID®, ZANTAC®, PROTONIX® may have wide-ranging systemic effects, such as motility disorders, allergic reactions and diarrhea. Additionally, because of the systemic manner in which they affect the human organism, the treatment provided by and the various side effects produced by pharmaceutical products cannot be terminated instantaneously, but instead must be allowed to run their course until metabolized or otherwise eliminated by the body. Previous treatments employing electrical stimulation techniques have not applied stimulation to certain areas of the patient's digestive system for the purpose of lowering the acidity of gastric secretions, or for the purpose of lowering the amount of gastric secretions produced.

The gastrointestinal tract has an extensive nervous system of its own called the enteric nervous system. There are two main plexuses in the enteric system:
  (1) An outer plexus—called the myenteric plexus—that lies between the longitudinal and circular muscle layers, and;
  (2) An inner plexus—called the submucosal plexus—that lies in the submucosa.

The myenteric plexus primarily controls the gastrointestinal movements, and the submucosal plexus mainly controls gastrointestinal secretion and local blood flow. The sympathetic and parasympathetic fibers connect with both the plexuses, and can further activate or inhibit gastrointestinal function (see FIG. 5a).

More than a dozen neurotransmitters have been identified in the gastrointestinal tract. Acetylcholine (a parasympathetic neurotransmitter) typically excites gastrointestinal activity and norepinephrine (a sympathetic neurotransmitter) typically inhibits gastrointestinal activity.

The cranial parasympathetic fibers extensively innervate the stomach, and are transmitted almost entirely in the vagus nerves that run proximal to the esophagus. The sympathetic fibers to the gastrointestinal tract originate in the spinal cord between segments T-5 and L-2. Stimulation of these fibers result in an inhibitory effect by norepinephrine which can block movement of food through the gastrointestinal tract.

Many afferent sensory nerve fibers arise in the gut. These nerves can be stimulated by (1) irritation of the gut mucosa, (2) excessive distention of the gut, or (3) presence of specific chemical substances in the gut. Almost 80% of nerve fibers in the vagus bundle are afferent rather than efferent. These fibers transmit afferent signals into the medulla, which in turn initiates many reflex signals that control gastro-intestinal functions. As such, stimulation of the vagus nerve may directly affect the gastro-intestinal tract through efferent nerve capture or through a more circuitous route involving the medulla.

As shown in FIG. 5b, the wall of the stomach is lined with billions of single-cell mucous glands. These cells extrude mucous directly onto the epithelial surface to act as a lubricant and prevent auto-digestion. There are also two types of tubular glands that exist, the oxyntic glands and the pyloric glands. The oxyntic glands secrete hydrochloric acid (HCl) and the pyloric glands secrete the hormone gastrin. The oxyntic glands are located on the inside surfaces of the body and fundus of the stomach, and the pyloric glands are located in the antral portion of the stomach. Gastrin and histamine are potent stimulants for acid release by the parietal cells in the oxyntic glands; the parietal cells secrete a highly acidic solution that contains about 160 millimoles of HCl per liter. A synthetic form of gastrin known as pentagastrin is composed of the terminal four amino acids of natural gastrin plus the amino acid alanine. It has all the same physiological properties as natural gastrin.

It has been shown that relatively slow stimulation of the vagi (4-8 Hz) induces maximal acid secretion in cats (Sjodin, 1975). Pharmaceutical companies frequently use this model to test acid-suppressing drugs. Grundy and Scratcherd, however, found that higher rate electrical stimulation (120 Hz) of the vagus nerve significantly reduced acid production versus basal output in ferrets. In their experiment, they performed a bilateral vagotomy in the neck and stimulated the thoracic vagi via a left thoracotomy. The stimulation regime they applied was "physiologic" (a taped replica of natural vagal activity), "burst" (60 or 120 Hz, 500 microsecond pulse width), or "continuous" (6 Hz). Their data showed that continuous low-rate stimulation increased acid output relative to the "taped" physiologic stimulation, while burst stimulation significantly decreased acid output.

Some prior art publications relating to the present invention are as follows:

Kenneth Koch et al., "An Illustrated Guide To Gastrointestinal Motility," Electrogastrography, 2nd Ed., pp. 290-307 (1993).

Kenneth Koch et al., "Functional Disorders of the Stomach," Seminars in Gastrointestinal Disease, Vol. 7, No. 4, 185-195 (October 1996).

Kenneth Koch, "Gastroparesis: Diagnosis and Management," Practical Gastroenterology (November 1997).

Babajide Familoni et al., "Efficacy of Electrical Stimulation at Frequencies Higher than Basal Rate in Mayine Stomach," Digestive Diseases and Sciences, Vol. 42, No. 5 (May 1997).

Babajide O. Familoni, "Electrical Stimulation at a Frequency Higher than Basal Rate in Human Stomach," Digestive Diseases and Sciences, Vol. 42, No. 5 (May 1997).

Grundy, D. and Scratcherd, T., "Effects of stimulation of the vagus nerve in bursts on gastric acid secretion and motility in the anaesthetized ferret," *J. Physiol.*, 333: 451-461, 1982.

Sasaki, N., et al., "Selective action of a CCK-B/gastrin receptor antagonist, S-0509, on pentagastrin-, peptone meal- and beer-stimulated gastric acid secretion in dogs," Aliment. Pharmacol. Ther., 14: 479-488, 2000.

Sjodin, L., "Gastric acid responses to graded vagal stimulation in the anaesthetized cat," Digestion, 12(1): 17-24, 1975.

Physician's Manual, NeuroCyberonics Prosthesis, Bipolar Lead, Model 300, September, 2001.

U.S. Pat. No. 5,188,104 to Wernicke et al. for "Treatment of Eating Disorders by Nerve Stimulation."

U.S. Pat. No. 5,231,988 to Wernicke et al. for "Treatment of Endocrine Disorders by Nerve Stimulation."

U.S. Pat. No. 5,263,480 to Wernicke et al. for "Treatment of Eating Disorders by Nerve Stimulation."

U.S. Pat. No. 5,292,344 to Douglas for "Percutaneously placed electrical gastrointestinal pacemaker INSy system, sensing system, and pH monitoring system, with optional delivery port."

U.S. Pat. No. 5,423,872 to Cigaina for "Process and Device for Treating Obesity and Syndrome Motor Disorders of the Stomach of a Patient."

U.S. Pat. No. 5,540,730 to Terry for "Treatment of motility disorders by nerve stimulation."

U.S. Pat. No. 5,690,691 to Chen for "Gastro-intestinal pacemaker having phased multi-point stimulation."

U.S. Pat. No. 5,716,385 to Mittal for "Crural diaphragm pacemaker and method for treating esophageal reflux disease."

U.S. Pat. No. 5,836,994 to Bourgeois for "Method and apparatus for electrical stimulation of the gastrointestinal tract."

U.S. Pat. No. 5,925,070 to King et al. for "Techniques for adjusting the locus of excitation of electrically excitable tissue."

U.S. Pat. No. 5,941,906 to Barreras et al. for "Implantable, modular tissue INS."

U.S. Pat. No. 6,083,249 to Familoni for "Apparatus for sensing and stimulating gastrointestinal tract on-demand"

U.S. Pat. No. 6,097,984 to Douglas for "System and method of stimulation for treating gastro-esophageal reflux disease."

U.S. Pat. No. 6,238,423 to Bardy for "Apparatus and method for treating chronic constipation."

U.S. Pat. No. 6,381,496 to Meadows et al. for "Parameter context switching for an implanted device."

U.S. Pat. No. 6,393,325 to Mann et al. for "Directional programming for implantable electrode arrays."

U.S. Pat. No. 6,449,511 to Mintchev for "Gastrointestinal electrical INS having a variable electrical stimulus."

U.S. Pat. No. 6,453,199 to Kobosev for "Electrical Gastro-Intestinal Tract INS."

U.S. Pat. No. 6,516,227 to Meadows et al. for "Rechargeable spinal cord INS system."

U.S. Patent Application Publication No. 2002 165589 for "Gastric Treatment and Diagnosis Device and Method."

U.S. Patent Application Publication No. 2003 014086 for "Method and Apparatus for Electrical Stimulation of the Lower Esophageal Sphincter."

U.S. Patent Application Publication No. 2002 116030 for "Electrical stimulation of the Sympathetic Nerve Chain."

U.S. Patent Application Publication No. 2002 193842 for "Heartburn and Reflux Disease Treatment Apparatus."

U.S. Patent Application Publication No. 2002 103424 for "Implantable Medical Device Affixed Internally within the Gastrointestinal Tract."

U.S. Patent Application Publication No. 2002 198470 for "Capsule and Method for Treating or Diagnosing the Intestinal Tract."

PCT Patent Application WO 0089655 for "Sub-Mucosal Gastric Implant Device and Method."

PCT Patent Application WO 0176690 for "Gastrointestinal Electrical Stimulation."

PCT Patent Application WO 02087657 for "Gastric Device and Suction Assisted Method for Implanting a Device on a Stomach Wall."

PCT Patent Application WO 0238217 for "Implantable Neuromuscular INS for Gastrointestinal Disorders."

All patents and technical papers listed hereinabove are hereby incorporated by reference herein, each in its respective entirety. As those of ordinary skill in the art will appreciate readily upon reading the Summary of the Invention, Detailed Description of the Preferred Embodiments and claims set forth below, at least some of the devices and methods disclosed in the patents and publications listed hereinabove may be modified advantageously in accordance with the teachings of the present invention. The foregoing and other objects, features and advantages, which will now become more readily apparent by referring to the following specification, drawings and claims, are provided by the various embodiments of the present invention.

SUMMARY OF THE INVENTION

The present invention has certain objects. That is, various embodiments of the present invention provide solutions to one or more problems existing in the prior art respecting conventional treatment for gastric hyperacidity or excessive gastric acid production in a patient, including one or more of: (a) sequelae or side-effects resulting from the administration of pharmaceutical products; (b) the requirement to purchase expensive pharmaceutical products on an on-going basis; (c) when administering pharmaceutical products, not having the ability to terminate or change instantaneously administration of the therapy; and (d) lack of positive response to the administration of pharmaceutical therapy.

Various embodiments of the present invention have certain advantages, including one or more of: (a) targeted delivery of therapy; (b) ability to change the therapy delivered on-demand or instantaneously; (c) multiple methods of feedback control for optimizing therapy (e.g., pH, sensed blood metabolite levels, patient activated, time-dependent (e.g., activate stimulation therapy at mealtime); (d) lower cost than pharmaceuticals; (e) potential for the delivery of superior therapy; and (f) the patient does not have to remember to take a drug daily or according to a daily regimen.

Various embodiments of the present invention have certain features, including, but not limited to, the following: One or more electrical stimulation signals are applied to one or more appropriate portions of a patient's digestive system, vagus nerve, and/or portions in the vicinity of either in an amount and manner effective to lower the amount of a patient's gastric acid secretions and/or to lower the acidity of such secretions. The at least one electrical stimulation signal is applied by an INS that has at least one medical electrical lead positionable, secured or attached to or in a patient's digestive system and/or vagus nerve, or in the vicinity thereof. Each such lead carries at least one electrode, and preferably at least two electrodes, positionable or attachable for contact with or in proximity to the patient's digestive system or vagus nerve. In one embodiment of the present invention, the electrical stimulation signal is adapted to reduce the amount or frequency of gastric acid secretions. In another embodiment of the present invention, the electrical stimulation signal is adapted to reduce the acidity of gastric secretions.

BRIEF DESCRIPTION OF THE DRAWINGS

These and other objects, features and advantages of the present invention will be more readily understood from the following detailed description of the preferred embodiments thereof, when considered in conjunction with the drawings, in which like reference numerals indicate identical structures throughout the several views, and wherein:

FIGS. 8a through 8d illustrate stimulation pulse, regime and control parameters according to some embodiments of the present invention;

The drawings are not necessarily to scale. Like numbers refer to like parts or steps throughout the drawings.

DETAILED DESCRIPTIONS OF EXEMPLARY EMBODIMENTS OF THE PRESENT INVENTION

Figure 1A:
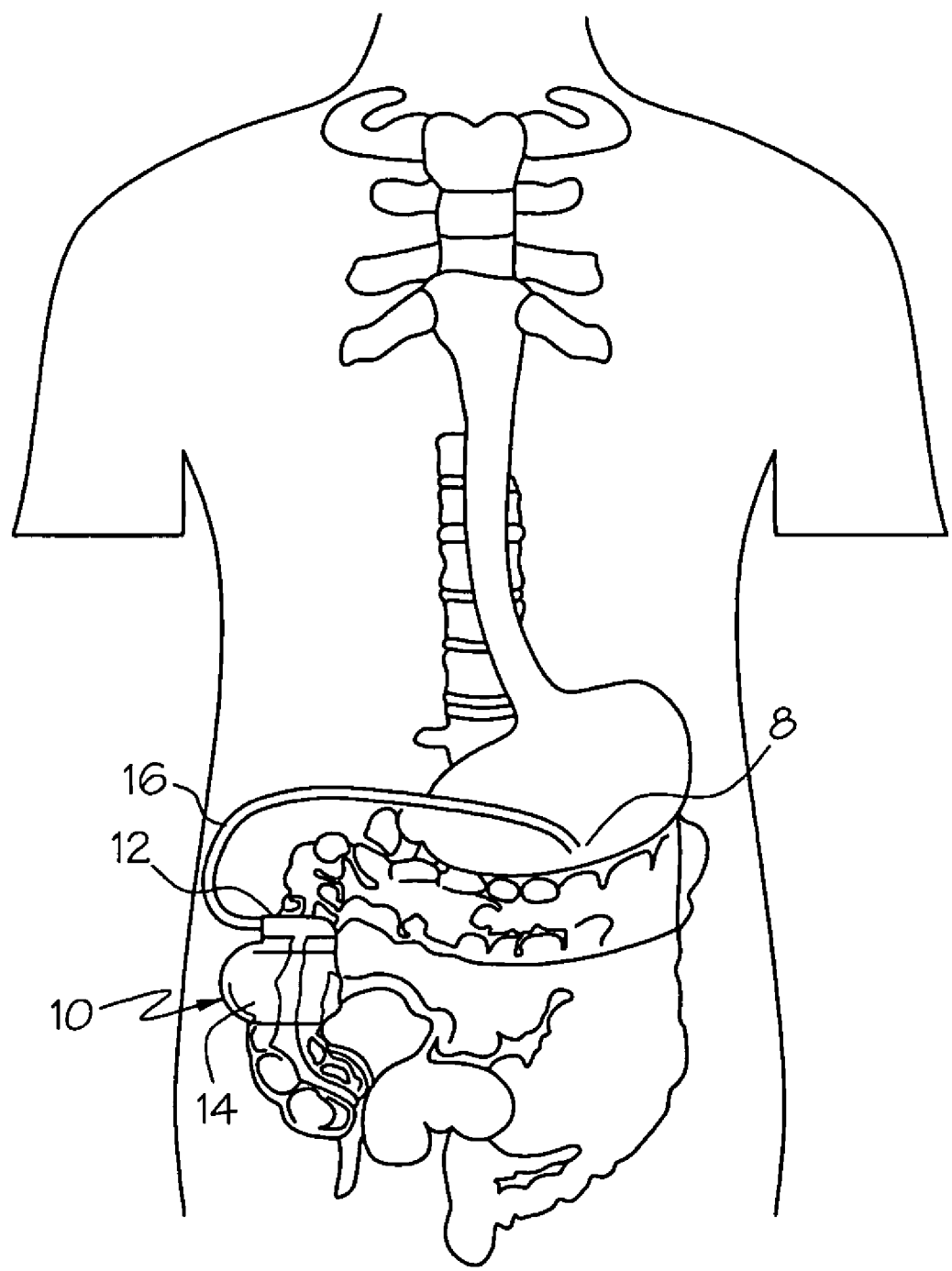
FIG. 1a illustrates one suitable arrangement for implanting one embodiment of a gastro-electric stimulation system of the present invention.
Figure 1B:
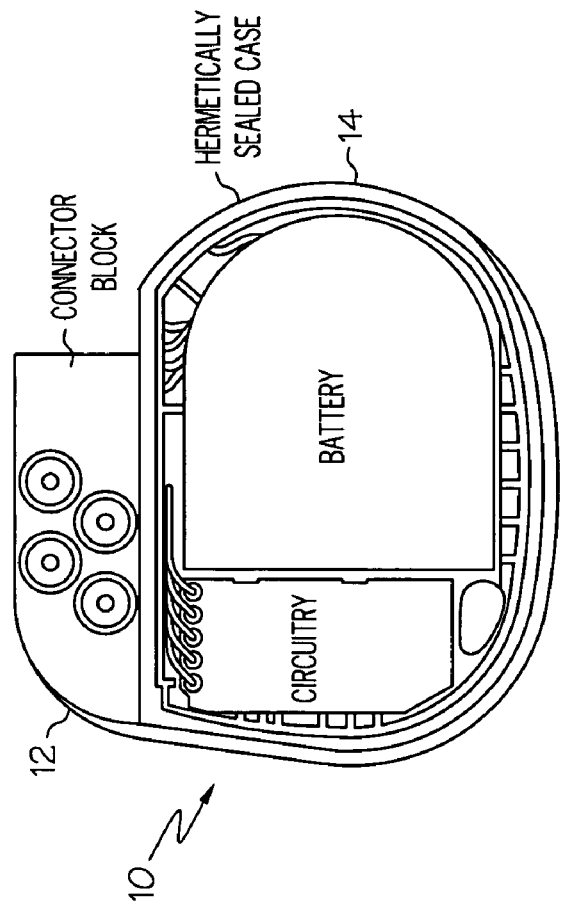
FIG. 1b shows illustrative components of one embodiment of a gastro-electric stimulation system of the present invention.
Figure 1B:
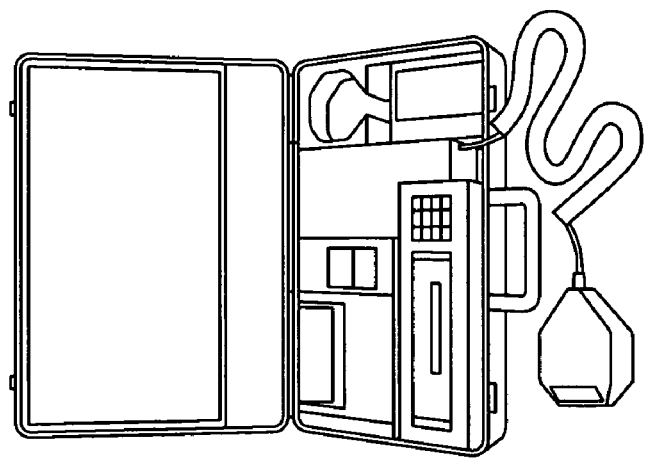
Figure 1B:
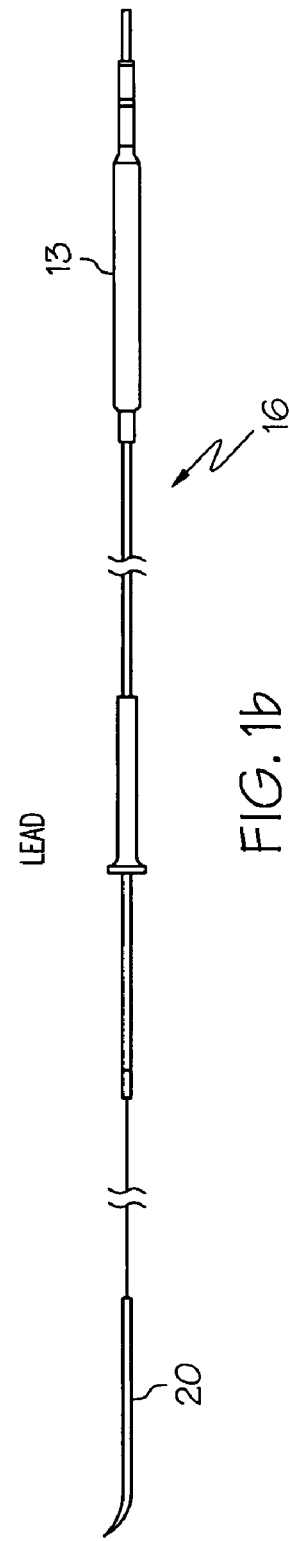
Figure 1C:
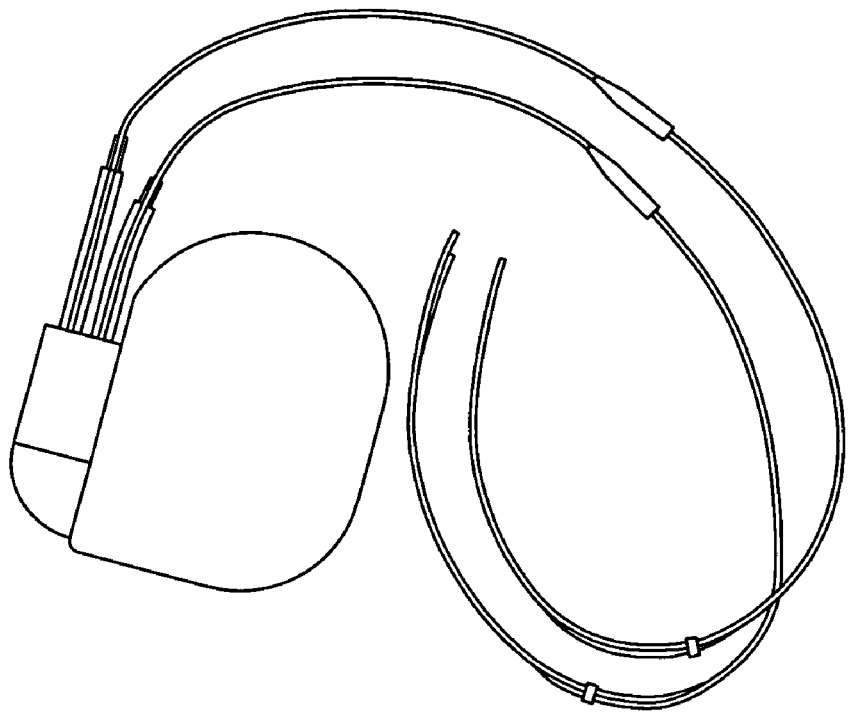
FIG. 1c shows an illustrative INS and associated medical electrical leads according to one embodiment of the present invention.

In the following descriptions of the preferred embodiments, reference is made to the accompanying drawings that form a part hereof, and in which are shown by way of illustration several specific embodiments of the invention. It is to be understood that other embodiments of the present invention are contemplated and may be made without departing from the scope or spirit of the present invention. The following detailed description, therefore, is not to be taken in a limiting sense. Instead, the scope of the present invention is to be defined in accordance with the appended claims.

In the present invention, electrical stimulation of appropriate portions of the vagus nerve and/or the digestive system, more about which we say below, influences the amount and/or frequency of gastric acid secretions, and may also be employed to reduce the acidity of such secretions, leading to an overall increase in the pH of the gastric acid contained in a patient's stomach. Nerve impulses generated by electrical stimulation of appropriate portions of the vagus nerve and/or digestive system travel by means of both afferent and efferent pathways to cells in stomach lining which produce gastric acid. Some impulses may travel from the digestive system along a vagal afferent pathway to the brain and then along a vagal efferent pathway from the brain to the stomach lining. Various portions of the stomach in the digestive system are well suited for stimulation in accordance with some embodiments of the present invention. For example, the wall of the stomach is suitable for making electrical connections and the stomach is well innervated by the vagus nerve, and the stomach pacemaker region is particularly well innervated by the vagus nerve and other portions of the digestive system.

FIG. 1 further shows one embodiment of INS 10 of the present invention having a lead positioned near a desired or target nerve or nerve portion 8. INS 10 shown in FIG. 1 is a implantable electrical stimulator comprising at least one implantable medical electrical lead 16 attached to hermetically sealed enclosure 14, lead 16 being implanted near desired or target nerve or nerve portion 8. Enclosure 14 is formed of a biocompatible material such as an appropriate metal alloy containing titanium. It is important to note that at least one more lead 18 (not shown in the drawings) may be employed in accordance with certain embodiments of the present invention, where multiple nerve target sites or portions are to be stimulated simultaneously or sequentially and/or where such multiple target sites or portions are incapable of being stimulated, or are difficult to stimulate, using a single lead even if the single lead contains multiple stimulation electrodes or arrays of stimulation electrodes. FIG. 1c shows an illustrative INS and associated medical electrical leads according to one embodiment of the present invention.

Referring now to FIG. 1b and FIGS. 4a through 4f, lead 16 provides electrical stimulation pulses to the desired nerve target sites or portions and thereby inhibits or excites signals originating in or carried by a desired or target nerve or nerve portion located in the vicinity of the electrode(s) thereof. Leads 16 and lead 18 may have unipolar electrodes disposed thereon (where enclosure 14 is employed as an indifferent electrode) or may have bipolar electrodes disposed thereon, where one or more electrodes disposed on a lead are employed as the indifferent electrode. In one embodiment of the present invention, lead 16 extends from lead connector 13, which in turn forms an integral portion of lead extension 15 connected at its proximal end to connector header module 12.

Leads 16 and 18 are preferably less than about 5 mm in diameter, and most preferably less than about 1.5 mm in diameter. Polyurethane is a preferred material for forming the lead body of leads 16 and 18, although other materials such as silicone may be employed. Electrical conductors extending between the proximal and distal ends of leads 16 and 18 for supplying electrical current to the electrodes are preferably formed of coiled, braided or stranded wires comprising an MP35N platinum-iridium alloy. Electrodes 20, 21, 22 and 23 may be ring electrodes, coiled electrodes, electrodes formed from portions of wire, barbs, hooks, spherically-shaped members, helically-shaped members, or may assume any of a number of different structural configurations well known in the art.

Inter-electrode distances on leads 16 and 18 are preferably about 3 mm, but other inter-electrode distances may be employed such as about 1 mm, about 2 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, about 30 mm. Preferred surface areas of electrodes 20, 21, 22 and 23 range between about 1.0 sq. mm and about 100 sq. mm, between about 2.0 sq. mm and about 50 sq. mm, and about 4.0 sq. mm and about 25 sq. mm. Preferred lengths of electrodes 20, 21, 22 and 23 range between about 0.25 mm and about 10 mm, between about 0.50 mm and about 8 mm, and about 1.0 mm and about 6 mm. Electrodes 20, 21, 22 and 23 are preferably formed of platinum, although other metals and metal alloys may be employed such as stainless steel or gold.

The distal portion of lead 16 extends to a target site or position near a desired nerve or nerve portion 8, and is preferably held in such position by lead anchor 19. Note that lead anchor 19 may assume any of a number of different structural configurations such one or more suture sleeves, tines, barbs, hooks, a helical screw, tissue in-growth mechanisms, adhesive or glue.

One, two, three, four or more electrodes 20, 21, 22 and 23 may be disposed at the distal end of lead 16 and/or lead 18. Electrodes 20, 21, 22 and 23 are preferably arranged in an axial array, although other types of arrays may be employed such as inter-lead arrays of electrodes between the distal ends of leads 16 and 18 such that nerves or nerve portions 8 disposed between leads 16 and 18 may be stimulated. Electrode configurations, arrays and stimulation patterns and methods similar to those disclosed by Holsheimer in U.S. Pat. No. 6,421,566 entitled "Selective Dorsal Column Stimulation in SCS, Using Conditioning Pulses," U.S. Pat. No. 5,643,330 entitled "Multichannel Apparatus for Epidural Spinal Cord Stimulation" and U.S. Pat. No. 5,501,703 entitled "Multichannel Apparatus for Epidural Spinal Cord INS," the respective entireties of which are hereby incorporated by reference herein, may also be adapted or modified for use in the present invention. Electrode configurations, arrays, leads, stimulation patterns and methods similar to those disclosed by Thompson in U.S. Pat. No. 5,800,465 entitled "System and Method for Multisite Steering of Cardiac Stimuli," the entirety of which is hereby incorporated by reference herein, may also be adapted or modified for use in the present invention to permit the steering of electrical fields. Thus, although the Figures show certain electrode configurations, other lead locations and electrode configurations are possible and contemplated in the present invention.

Leads 16 and 18 preferably range between about 4 inches and about 20 inches in length, and more particularly may be about 6 inches, about 8 inches, about 10 inches, about 12 inches, about 14 inches, about 16 inches or about 18 inches in length, depending on the location of the site to be stimulated and the distance of INS 10 from such site. Other lead lengths such as less than about 4 inches and more than about 20 inches are also contemplated in the present invention.

Typically, leads 16 and 18 are tunneled subcutaneously between the location of INS 10 and the location or site of the nerve or nerve portion that is to be stimulated. INS 10 is typically implanted in a subcutaneous pocket formed beneath the patient's skin according to methods well known in the art. Further details concerning various methods of implanting INS 10 and leads 16 and 18 are disclosed in the Medtronic Interstim Therapy Reference Guide published in 1999, the entirety of which is hereby incorporated by reference herein. Other methods of implanting and locating leads 16 and 18 are also contemplated in the present invention.

U.S. patent application Ser. Nos. 10/004,032 entitled "Implantable Medical Electrical Stimulation Lead Fixation Method and Apparatus" now U.S. Pat. No. 6,999,819, and Ser. No. 09/713,598 entitled "Minimally Invasive Apparatus for Implanting a Sacral Stimulation Lead" to Mamo et al., now U.S. Pat. No. 6,971,393, the respective entireties of which are hereby incorporated by reference herein, describe methods of percutaneously introducing leads 16 and 18 to a desired nerve stimulation site in a patient.

Some representative examples of leads 16 and 18 include MEDTRONIC nerve stimulation lead model numbers 3080, 3086, 3092, 3487, 3966 and 4350 as described in the MEDTRONIC Instruction for Use Manuals thereof, all hereby incorporated by reference herein, each in its respective entirety. Some representative examples of INS 10 include MEDTRONIC implantable electrical INS model numbers 3023, 7424, 7425 and 7427 as described in the Instruction for Use Manuals thereof, all hereby incorporated by reference herein, each in its respective entirety. See also FIGS. 4b through 4f hereof, which disclose various embodiments of leads 16 and 18 suitable for use in accordance with the present invention. INS 10 may also be constructed or operate in accordance with at least some portions of the implantable INSs disclosed in U.S. Pat. No. 5,199,428 to Obel et al., U.S. Pat. No. 5,207,218 to Carpentier et al. or U.S. Pat. No. 5,330,507 to Schwartz, all of which are hereby incorporated by reference herein, each in its respective entirety.

Lead locations and electrode configurations other than those explicitly shown and described here are of course possible and contemplated in the present invention. Lead anchors 19 are shown in FIG. 4c as a series of tines.

FIG. 1 shows the general environment of a gastro-electric stimulation system of the present invention. The patient depiction shows an abdomen, a digestive system, a stomach, a duodenum, an intestine, a pancreas, an enteric nervous system, and a vagus nerve. The gastro-electric stimulation system may be implanted, or may be located outside the patient. A programmer, separate from the gastro-electric stimulation system, may be used to modify parameters of the gastro-electric stimulation system. Programming may be accomplished with a console remote programmer such as a Model 7432 and Model 7457 memory module software or with a hand-held programmer such as an Itrel EZ, available from Medtronic, Inc. of Minneapolis, Minn.

Figure 2A:
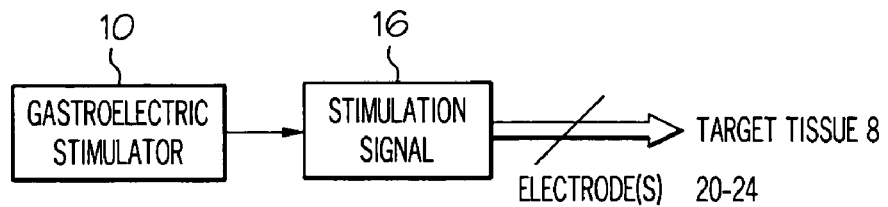
FIG. 2a shows a block diagram of one embodiment of an open-loop gastro-electric stimulation system of the present invention.
Figure 2B:
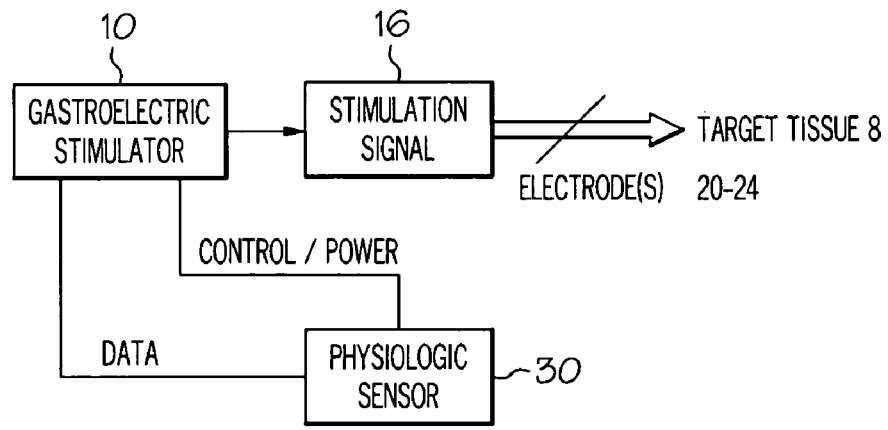
FIG. 2b shows a block diagram of one closed-loop embodiment of a gastro-electric stimulation system of the present invention.
Figure 2C:
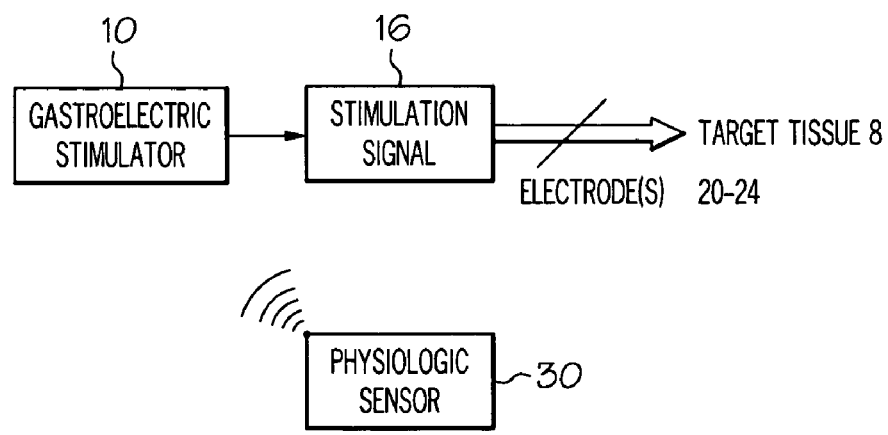
FIG. 2c shows a block diagram of another embodiment of a closed loop gastro-electric stimulation system of the present invention.

FIG. 2a shows a block diagram of one embodiment of an open-loop gastro-electric stimulation system of the present invention. FIG. 2b shows a block diagram of a closed-loop gastro-electric stimulation system. FIG. 2c shows a block diagram of yet another embodiment of a closed loop gastro-electric stimulation system of the present invention having a wireless connection between physiologic sensor 30 and INS 10.

In a closed-loop embodiment of the present invention, the system is preferably configured such that INS 10 is temporarily disabled so as not to provide electrical stimulation signals to nerve site or portion 8 after sensor 30 has detected, for example, an increase in gastric acid pH values above an accepted normal pH value. See, for example, U.S. Pat. No. 6,097,984 to Douglas, hereby incorporated by reference herein, in its entirety. Physiologic sensor 30 may be any of a number of suitable sensor types, such as a pH sensor, or any other sensor capable of sensing changes in gastric acidity or changes in the frequency of gastric acid production such as chemical or molecular sensors. For example, the sensed parameter may be pH, sensed either in the esophagus or in the stomach, may be an agonist for gastric acid secretion (e.g., acetylcholine, histamine, gastrin), or may be an antagonist for gastric acid secretion (e.g., prostaglandin, somatostatin, EGF, proglumide).

Figure 2D:
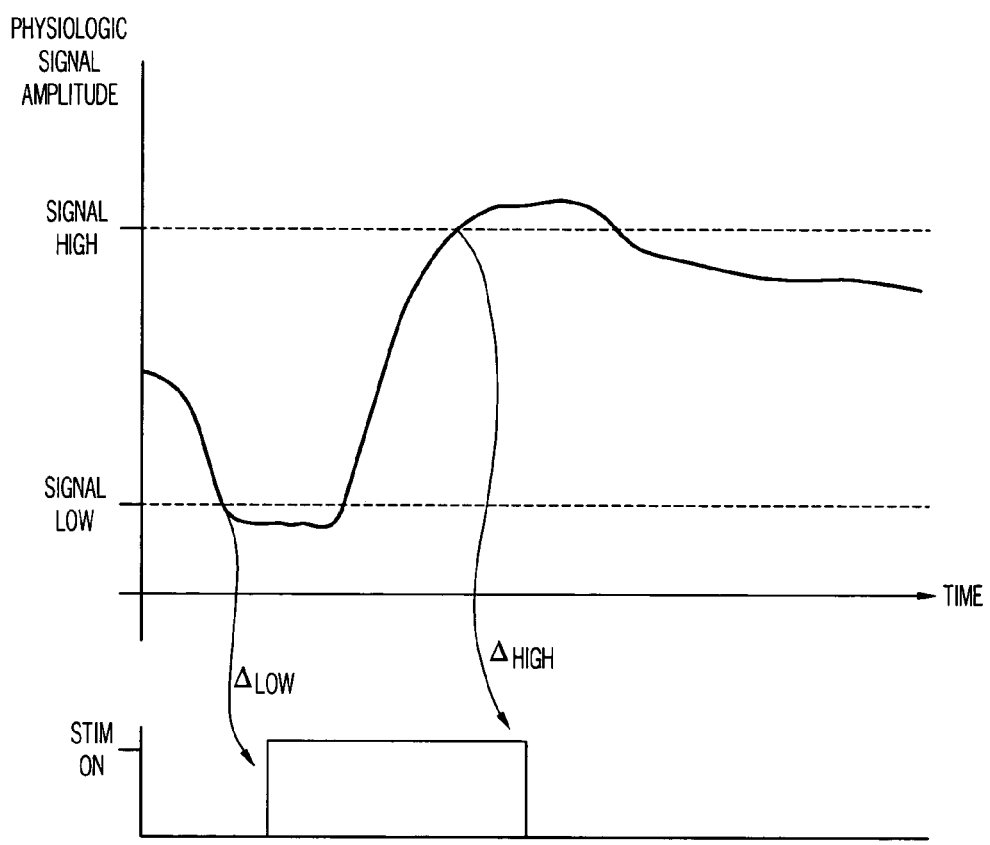
FIG. 2d shows a signal amplitude vs. time chart obtained in accordance with the present invention.

FIG. 2d shows an illustrative signal amplitude vs. time chart obtained in accordance with the present invention in respect of physiologic sensor 30 and the output signal generated thereby as a function of time. In such a closed-loop feedback control embodiment of the present invention, sensor 30 and sensing and computing circuitry in INS 10 cooperate to detect when a sensed signal has fallen below or risen above a predetermined threshold, as the case may be. Once the sensed signal has remained above or below the predetermined threshold for a predetermined period of time, stimulating circuitry in INS 10 is disabled. Such stimulating circuitry in INS 10 is subsequently enabled or activated when the sensed signal has once again risen above or fallen below the same or a different predetermined threshold.

Some examples of sensor technology that may be adapted for use in some embodiments of the present invention include those disclosed in the following U.S. patents:

U.S. Pat. No. 5,640,764 for "Method of forming a tubular feed-through hermetic seal for an implantable medical device;"
U.S. Pat. No. 5,660,163 for "Glucose sensor assembly;"
U.S. Pat. No. 5,750,926 for "Hermetically sealed electrical feedthrough for use with implantable electronic devices;"
U.S. Pat. No. 5,791,344 for "Patient monitoring system;"
U.S. Pat. No. 5,917,346 for "Low power current to frequency converter circuit for use in implantable sensors;"
U.S. Pat. No. 5,957,958 for "Implantable electrode arrays;"
U.S. Pat. No. 5,999,848 for "Daisy chainable sensors and stimulators for implantation in living tissue;"
U.S. Pat. No. 6,043,437 for "Alumina insulation for coating implantable components and other microminiature devices;"
U.S. Pat. No. 6,088,608 for "Electrochemical sensor and integrity tests therefor;"
U.S. Pat. No. 6,259,937 for "Implantable substrate sensor."

Each of the foregoing patents is incorporated by reference herein, each in its respective entirety.

In another embodiment of the present invention, an overall therapy aimed at decreasing gastric acid production and/or increasing gastric acid pH may best be delivered by applying a gastric acid secretion "increase signal" for a period of time after a meal has been ingested by a patient. Feedback control algorithms and methods of the present invention may also employ sensing or determining one or more of a patient's rate of gastric acid secretion or production, duodenum salinity, gastric acid impedance, gastric acid electrical activity, motion, pain, weight, nausea, and/or vomiting. As outlined above, such patient conditions may be sensed, measured or determined using an appropriate sensor or sensors that generates a corresponding output signal which is routed to the input of INS 10 for use in controlling electrical stimulation signals. The patient's condition may also be measured by the patient or a physician, who then employs the measured condition to control the electrical stimulation signal output provided by INS 10.

Figure 3:
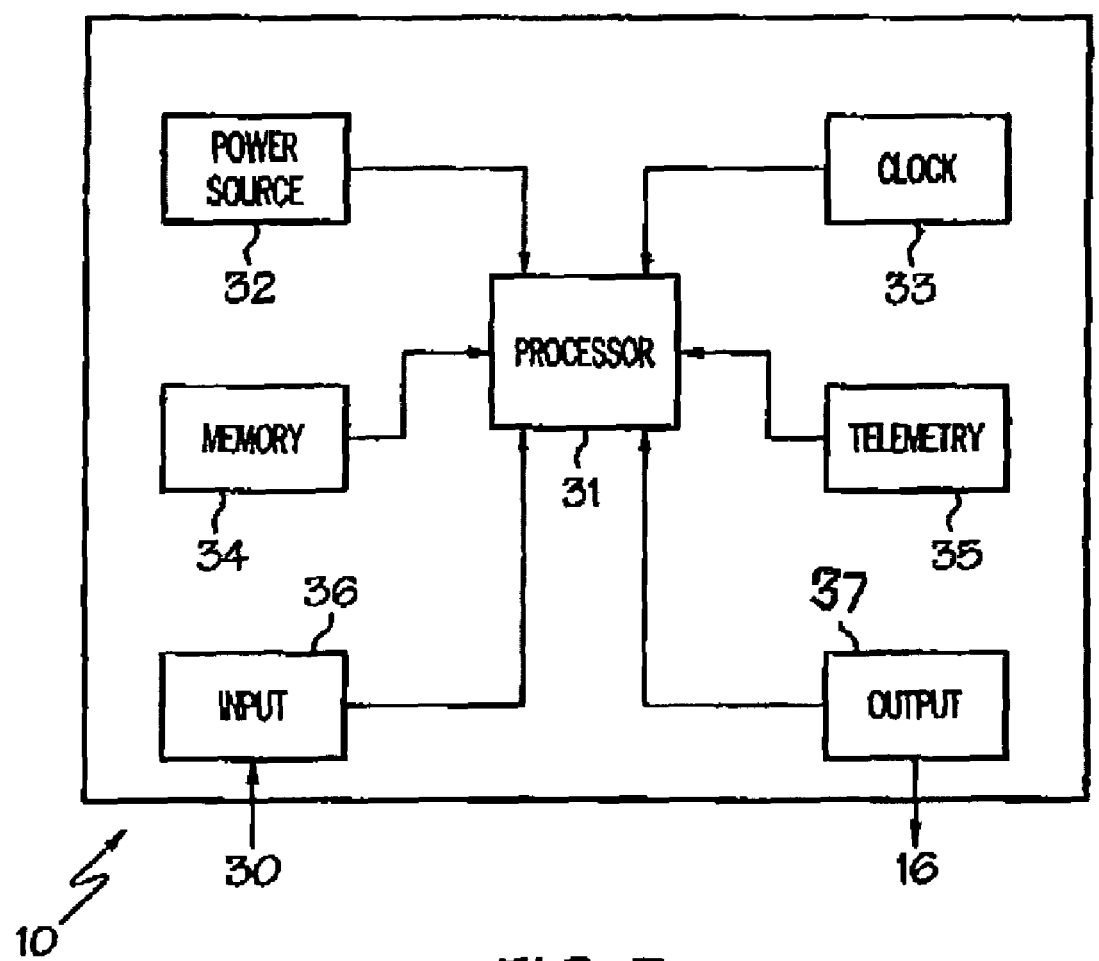
FIG. 3 shows a block diagram of one embodiment of the present invention.

FIG. 3 shows a block diagram illustrating some of the constituent components of INS 10 in accordance with one embodiment of the present invention, where INS 10 has a microprocessor-based architecture. Other architectures of INS 10 are of course contemplated in the present invention, such as the logic or state machine architecture employed in the Medtronic Model Number 3023 INS. For the sake of convenience, INS 10 in FIG. 3 is shown with only one lead 16 connected thereto; similar circuitry and connections not shown in FIG. 2 apply generally to lead 18 and other additional leads not shown in the drawings. INS 10 in FIG. 3 is most preferably programmable by means of external programming unit 11 shown in FIG. 1b. One such programmer is the commercially available Medtronic Model No. 7432 programmer, which is microprocessor-based and provides a series of encoded signals to INS 10, typically through a programming head which transmits or telemeters radio-frequency (RF) encoded signals to INS 10. Another suitable programmer is the commercially available Medtronic Model No. 8840 programmer, which is also microprocessor-based but features a touch control screen. Any of a number of suitable programming and telemetry methodologies known in the art may be employed so long as the desired information is transmitted to and from the implantable electrical INS 10.

As shown in FIG. 3, INS 10 receives input signals via physiologic sensor 30 and delivers output stimulation signals to lead 16. INS 10 most preferably comprises a CPU, processor, controller or micro-processor 31, power source 32 (most preferably a primary or secondary battery), clock 33, memory 34, telemetry circuitry 35, input 36 and output 37. Electrical components shown in FIG. 3 may be powered by an appropriate implantable primary (i.e., non-rechargeable) battery power source 32 or secondary (i.e., rechargeable) battery power source 32. INS 10 may also contain a battery or capacitor which receives power from outside the body by inductive coupling between an external transmitter and an implanted receiver. For the sake of clarity, the coupling of power source 32 to the various components of INS 10 is not shown in the Figures. An antenna is connected to processor 31 via a digital controller/timer circuit and data communication bus to permit uplink/downlink telemetry through RF transmitter and receiver telemetry unit 35. By way of example, telemetry unit 35 may correspond to that disclosed in U.S. Pat. No. 4,566, 063 issued to Thompson et al. It is generally preferred that the particular programming and telemetry scheme selected permit the entry and storage of electrical stimulation parameters. The specific embodiments of the antenna and other telemetry circuitry presented herein are shown for illustrative purposes only, and are not intended to limit the scope of the present invention.

An output pulse generator provides pacing stimuli to the desired nerve or nerve portion through, for example, a coupling capacitor in response to a trigger signal provided by a digital controller/timer circuit, when an externally transmitted stimulation command is received, or when a response to other stored commands is received. By way of example, an output amplifier of the present invention may correspond generally to an output amplifier disclosed in U.S. Pat. No. 4,476,868 to Thompson, hereby incorporated by reference herein in its entirety. The specific embodiments of such an output amplifier are presented for illustrative purposes only, and are not intended to be limiting in respect of the scope of the present invention. The specific embodiments of such circuits may not be critical to practicing some embodiments of the present invention so long as they provide means for generating an appropriate train of stimulating pulses to the desired nerve or nerve portion.

In various embodiments of the present invention, INS 10 may be programmably configured to operate so that it varies the rate at which it delivers stimulating pulses to the desired nerve or nerve portion 8 in response to one or more selected outputs being generated. INS 10 may further be programmably configured to operate so that it may vary the morphology of the stimulating pulses it delivers. Numerous implantable electrical INS features and functions not explicitly mentioned herein may be incorporated into INS 10 while remaining within the scope of the present invention. Various embodiments of the present invention may be practiced in conjunction with one, two, three or more leads, or in conjunction with one, two, three, four or more electrodes.

It is important to note that leadless embodiments of the present invention are also contemplated, where one or more stimulation and/or sensing electrode capsules or modules are implanted at or near a desired nerve stimulation site, and the capsules or modules deliver electrical stimuli directly to the site using a preprogrammed stimulation regime, and/or the capsules or modules sense electrical or other pertinent signals. Such capsules or modules are preferably powered by rechargeable batteries that may be recharged by an external battery charger using well-known inductive coil or antenna recharging means, and preferably contain electronic circuitry sufficient to permit telemetric communication with a programmer, to deliver electrical stimuli and/or sense electrical or other signals, and to store and execute instructions or data received from the programmer. Examples of methods and devices that may be adapted for use in the wireless devices and methods of the present invention include those described in U.S. Pat. No. 6,208,894 to Schulman et al. entitled "System of implantable devices for monitoring and/or affecting body parameters;" U.S. Pat. No. 5,876,425 to Schulman et al. entitled "Power control loop for implantable tissue stimulator;" U.S. Pat. No. 5,957,958 to Schulman et al. entitled "Implantable electrode arrays;" and U.S. patent application Ser. No. 09/030,106 filed Feb. 25, 1998 to Schulman et al. entitled "Battery-Powered Patient Implantable Device," all of which are hereby incorporated by reference herein, each in its respective entirety.

Figure 4A:
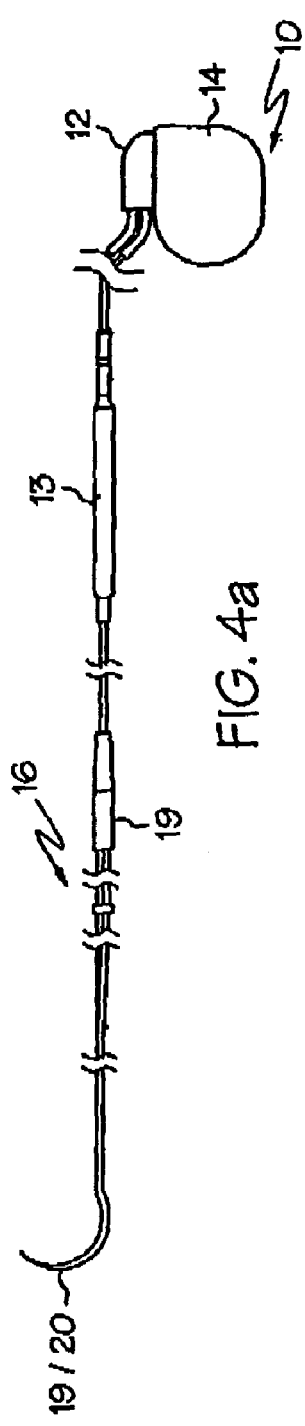
FIG. 4a shows one embodiment of a gastrointestinal stimulation system of the present invention.

FIG. 4a illustrates one embodiment of an implantable gastro-electric stimulation system suitable for use in the present invention, where the system comprises INS 10 and at least one associated medical electrical lead 16. INS 10 may be an implantable pulse generator (INS) such as a MEDTRONIC ITREL® 3 Model 7425 implantable INS, that produces or generates an electrical stimulation signals adapted for the purposes of the present invention. INS 10 may be surgically implanted such as in a subcutaneous pocket in the abdomen or positioned outside the patient. When positioned outside the patient, the INS 10 may be attached to the patient. INS 10 may be programmed to modify parameters of the delivered electrical stimulation signal such as frequency, amplitude, and pulse width in accordance with various embodiments of the present invention. By way of example, one or more leads 16 and 18 may be implanted into the muscle wall of the stomach such that lead electrodes 20 through 24 of adjacent leads are between about 0.5 cm apart to about 10.0 cm apart, and may be located proximal to the plexus where the vagus nerve joins the stomach.

Figure 4B:
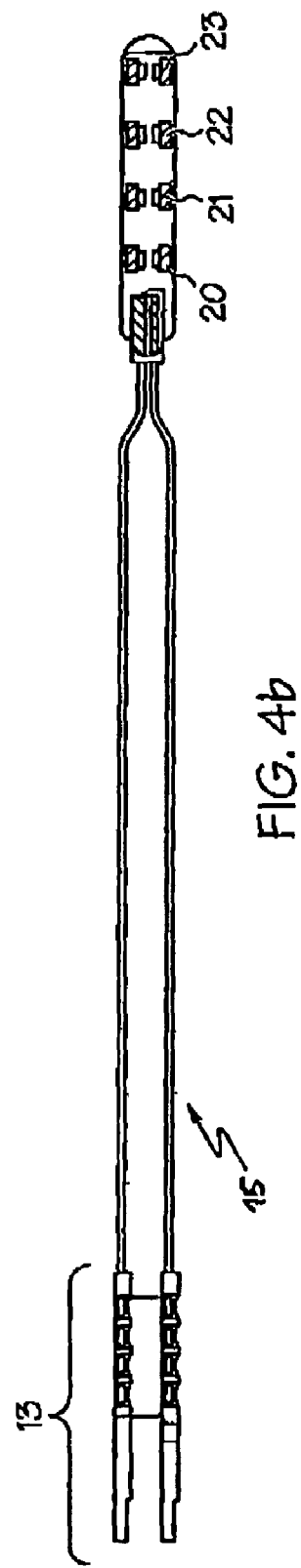
FIGS. 4b through 4f illustrate various embodiments of medical electrical leads suitable for use in the system of the present invention.
Figure 4C:
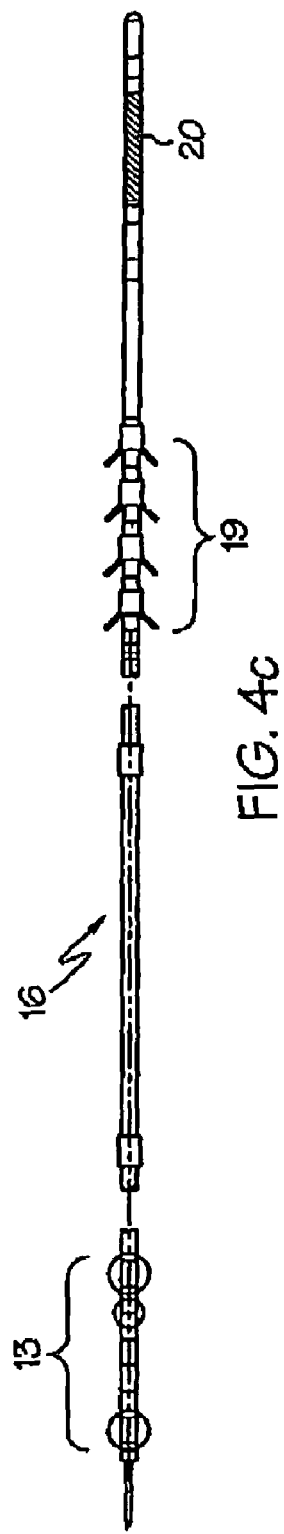
Figure 4D:
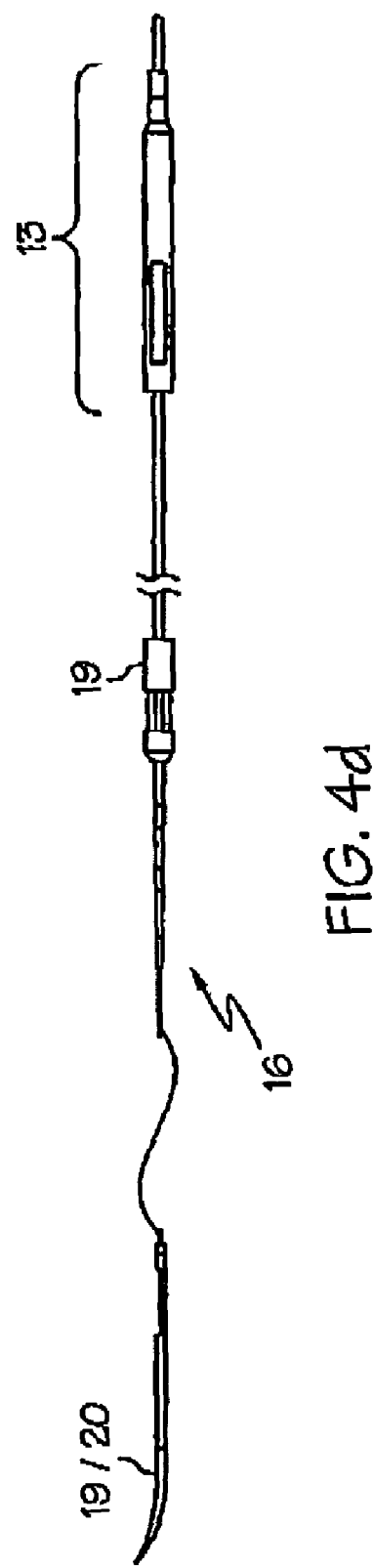
Figure 4E:
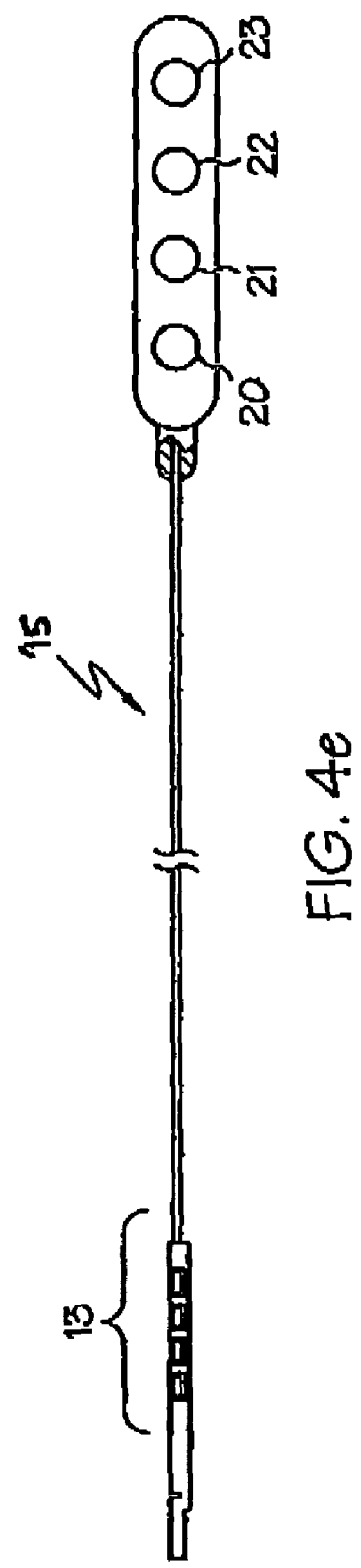

FIGS. 4b through 4f show various embodiments of the distal end of lead 16 of the present invention. In FIGS. 4b and 4e, lead 16 is a paddle lead where electrodes 20-23 are arranged along an outwardly facing planar surface. Such a paddle lead is preferably employed to stimulate peripheral nerves. In FIG. 4c, lead 16 is a conventional quadrapolar lead having no pre-attached anchoring mechanism where electrodes 20-23 are cylindrical in shape and extend around the circumference of the lead body. In FIG. 4d, lead 16 is a quadrapolar lead having tined lead anchors. The tines may be formed from flexible or rigid biocompatible materials in accordance with the application at hand. Representative examples of some tined and other types of leads suitable, adaptable or modifiable for use in conjunction with the systems, methods and devices of the present invention include those disclosed in U.S. patent application Ser. No. 10/004,732 entitled "Implantable Medical Electrical Stimulation Lead Fixation Method and Apparatus," now U.S. Pat. No. 6,999, 819 and Ser. No. 09/713,598 entitled "Minimally Invasive Apparatus for Implanting a Sacral Stimulation Lead" to Mamo et al., now U.S. Pat. No. 6,971,393 and those disclosed in U.S. Pat. No. 3,902,501 to Citron entitled "Endocardial Lead," U.S. Pat. No. 4,106,512 to Bisping entitled "Transvenously Implantable Lead," and U.S. Pat. No. 5,300,107 to Stokes entitled "Universal Tired Myocardial Pacing Lead," In FIG. 4d, lead 16 is a quadrapolar lead having a pre-attached suture anchor. In FIG. 4e, lead 16 comprises needle anchor/electrode 19/20 disposed at its distal end and suture anchor 19.

Figure 4F:
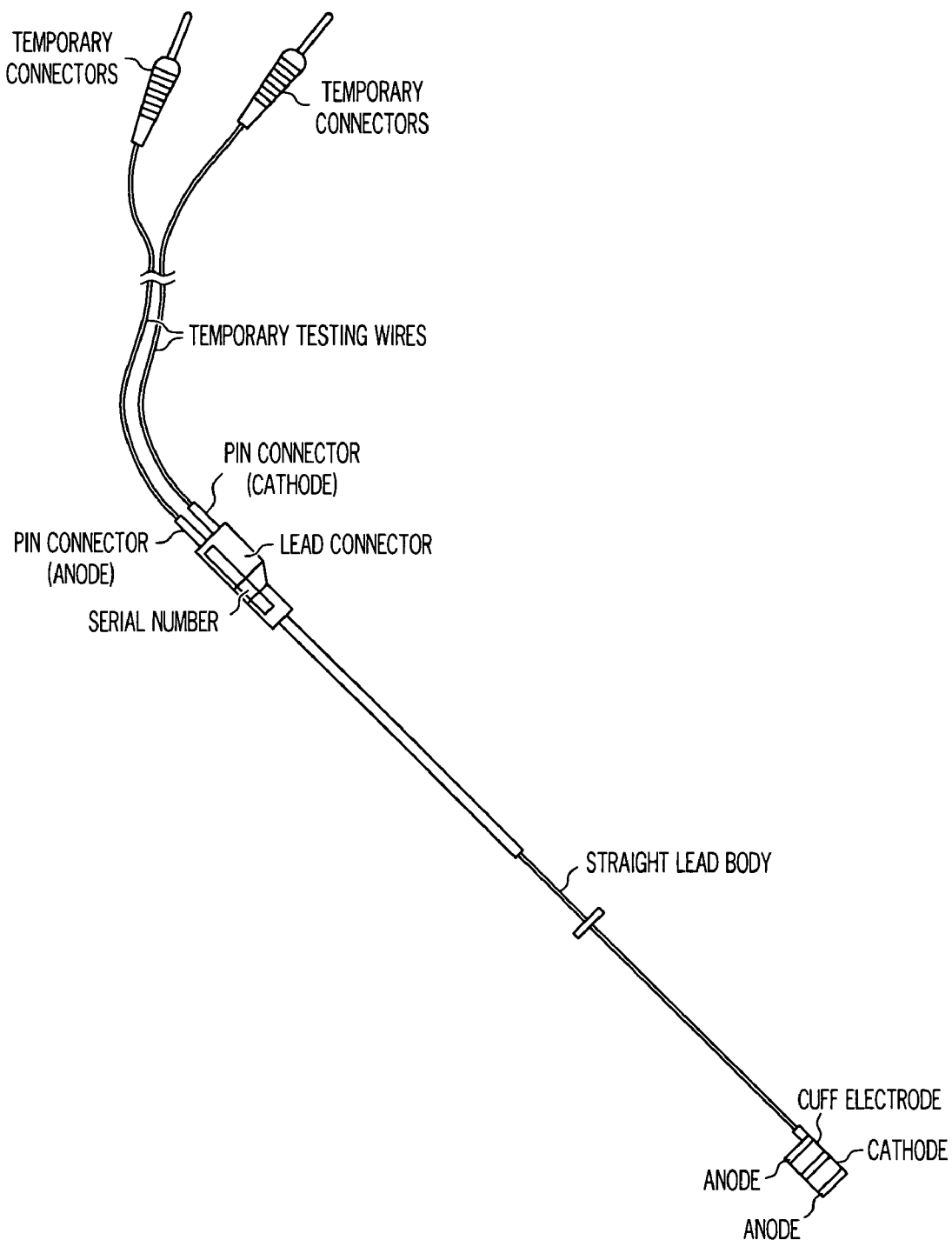
Figure 5A:
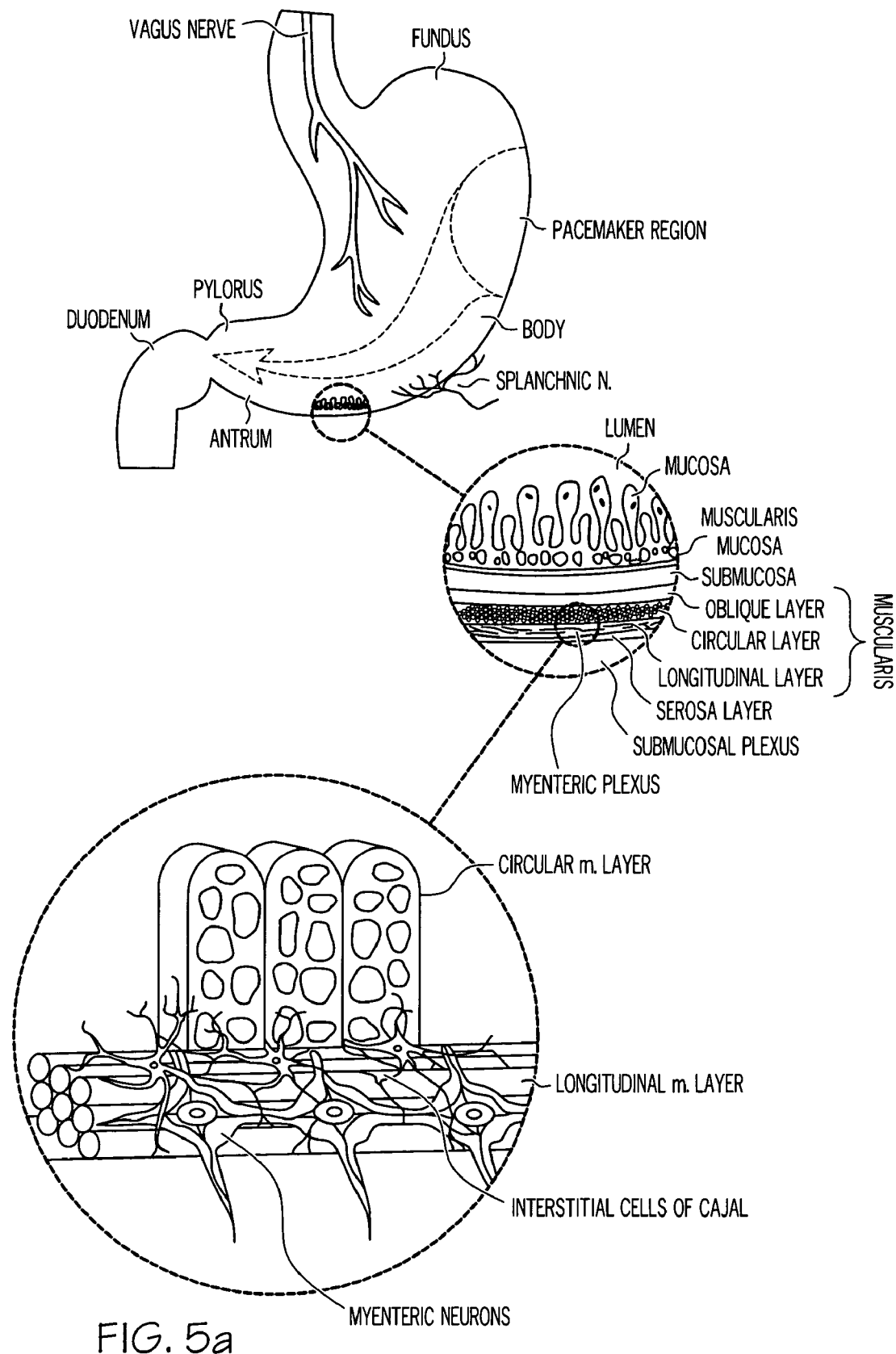
FIGS. 5a through 5d illustrate cross-sectional views of various portions of a patient's gastrointestinal tract and the nerve innervation and acid-production sites associated therewith.
Figure 5B:
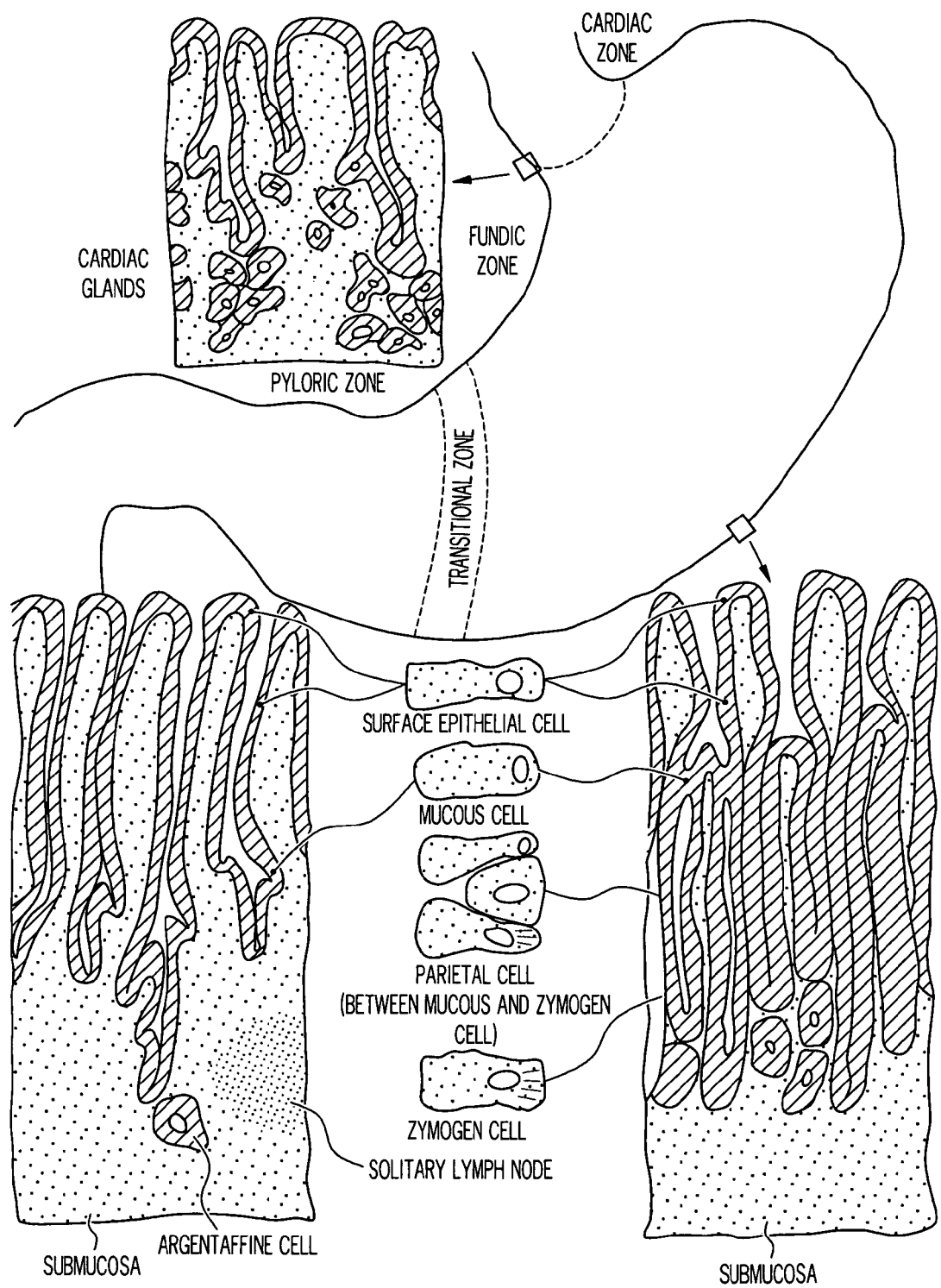
Figure 5C:
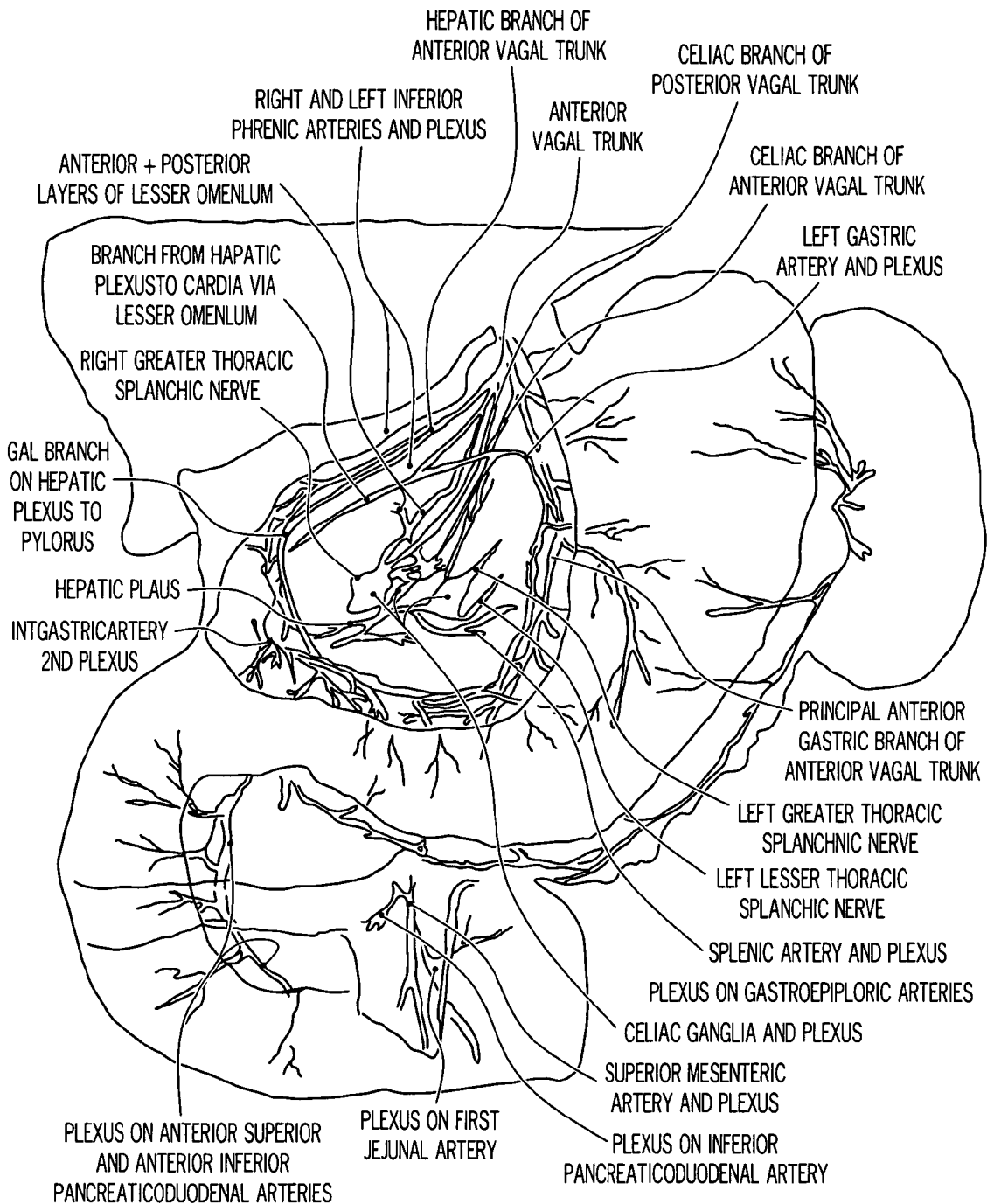
Figure 5D:
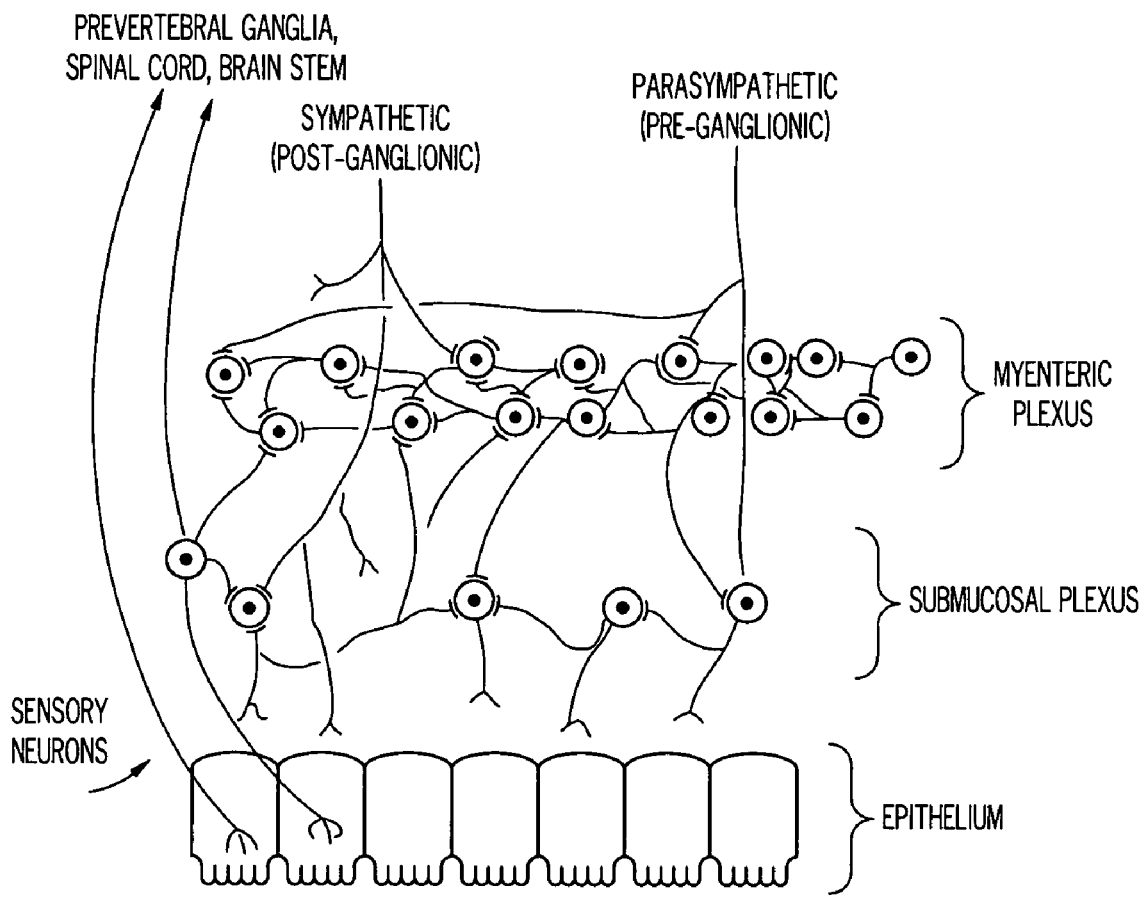
Figure 6A:
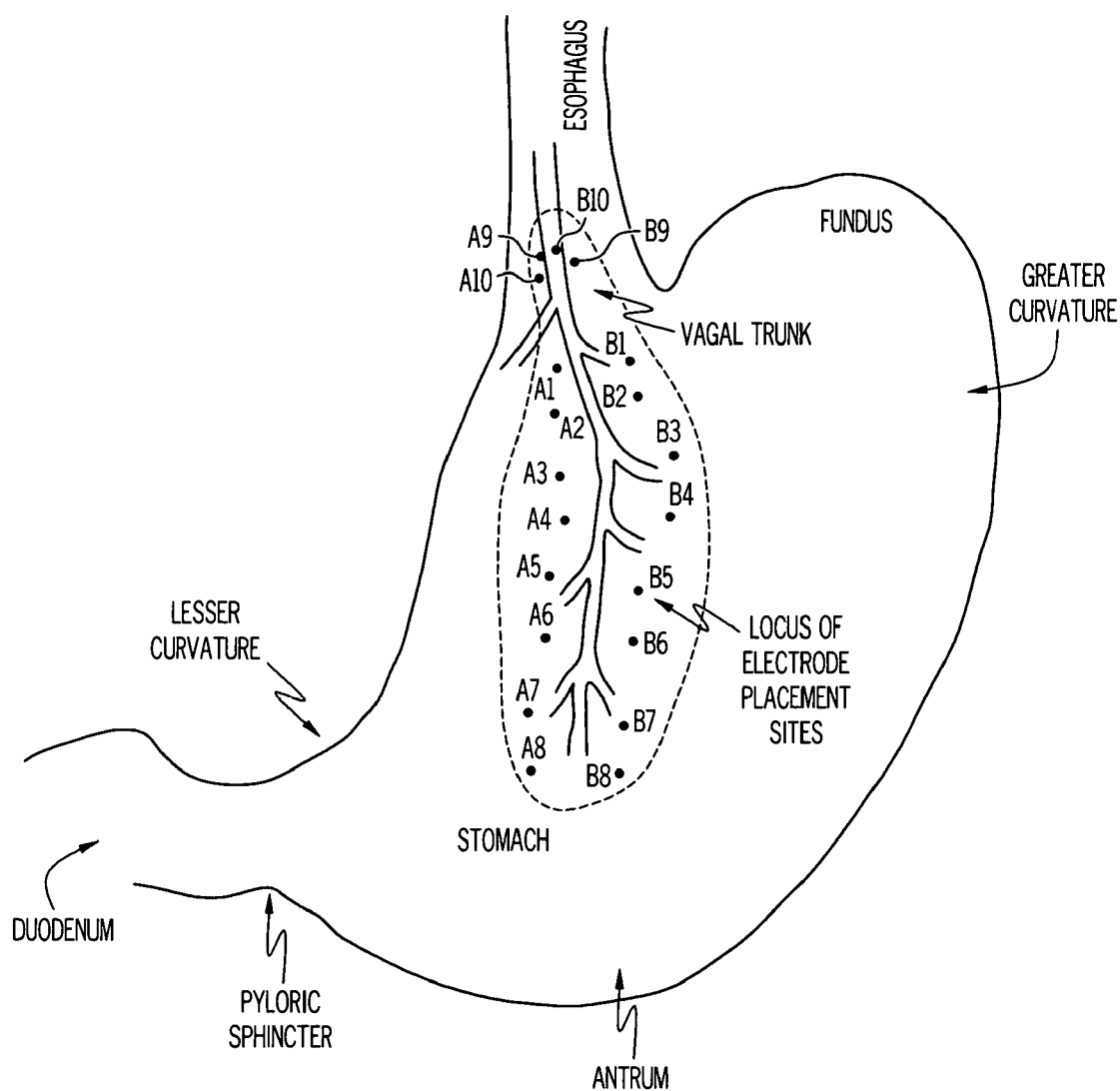
FIGS. 6a through 6f illustrate various electrode locations in or near the stomach and/or vagus nerve of a patient that may be stimulated and/or sensed in accordance with several embodiments of the present invention.
Figure 6B:
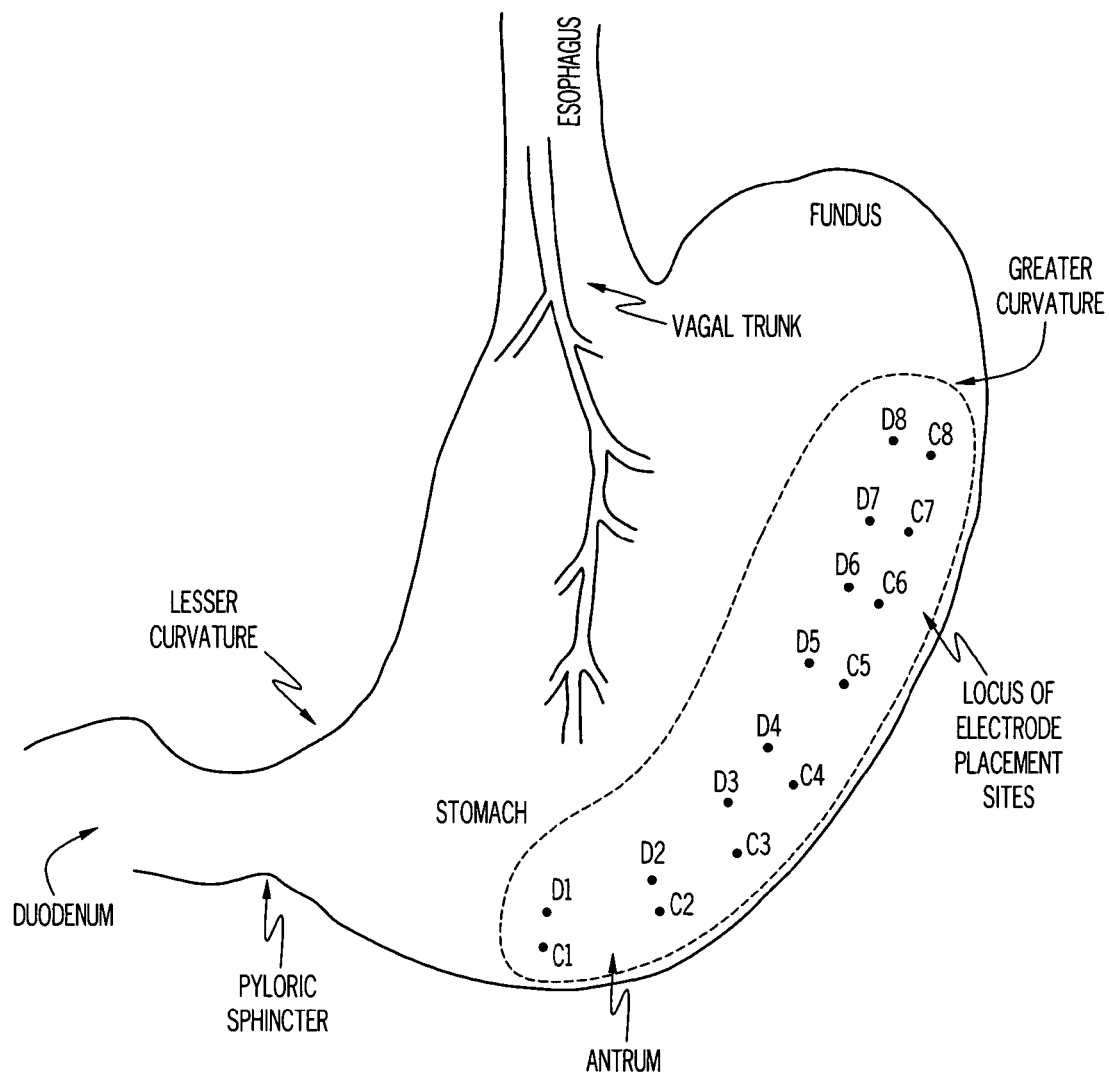
Figure 6C:
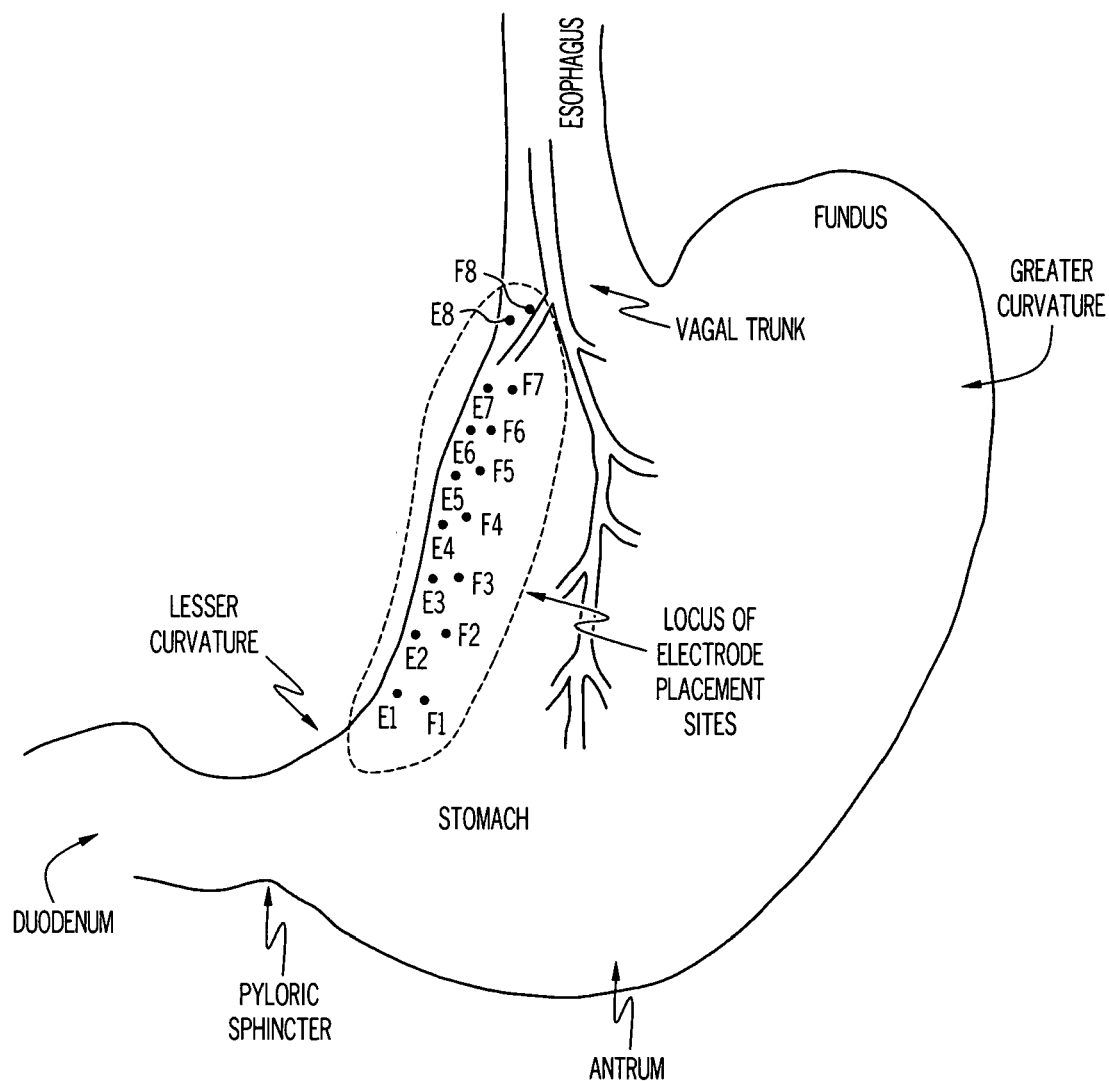
Figure 6D:
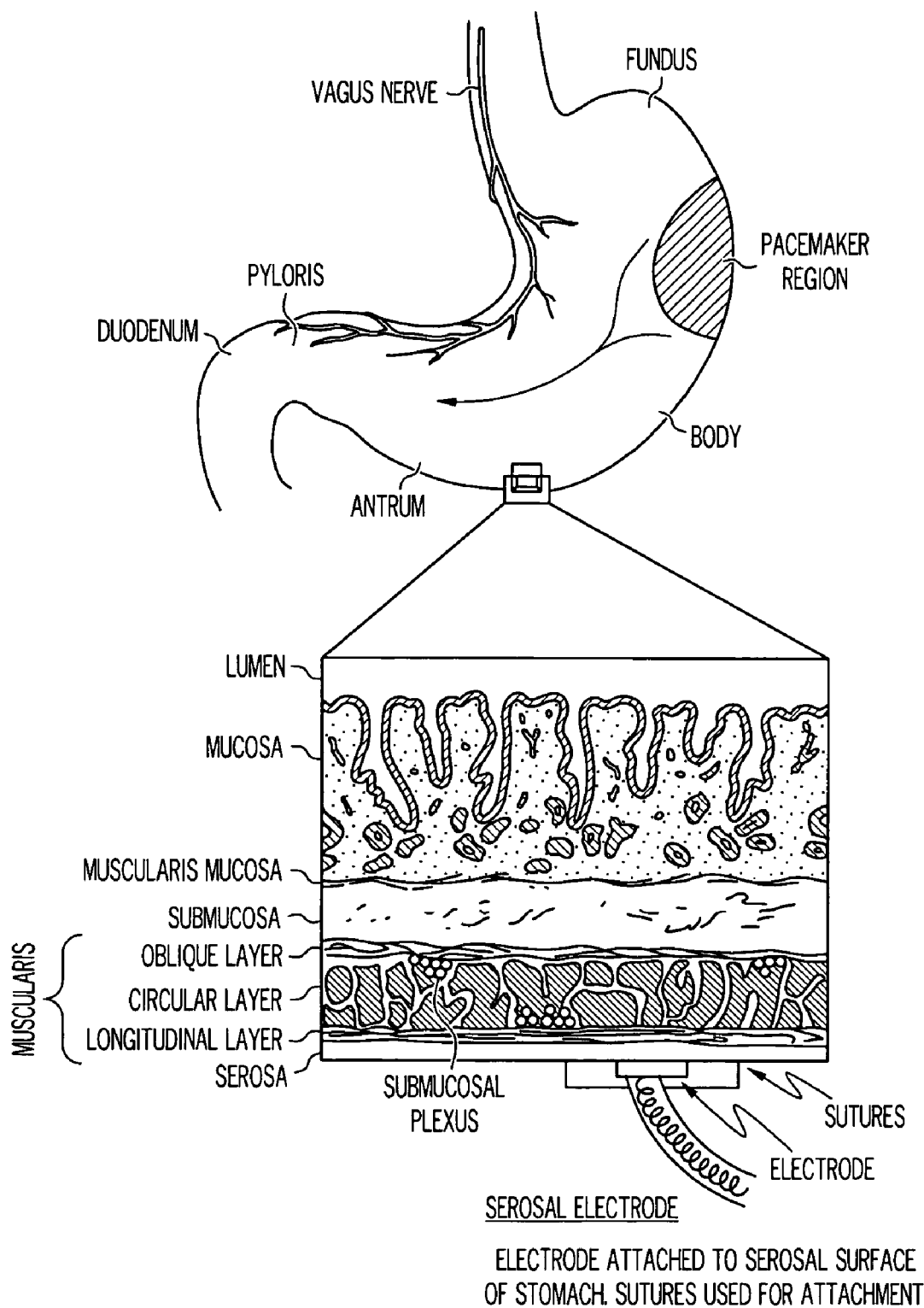
Figure 6E:
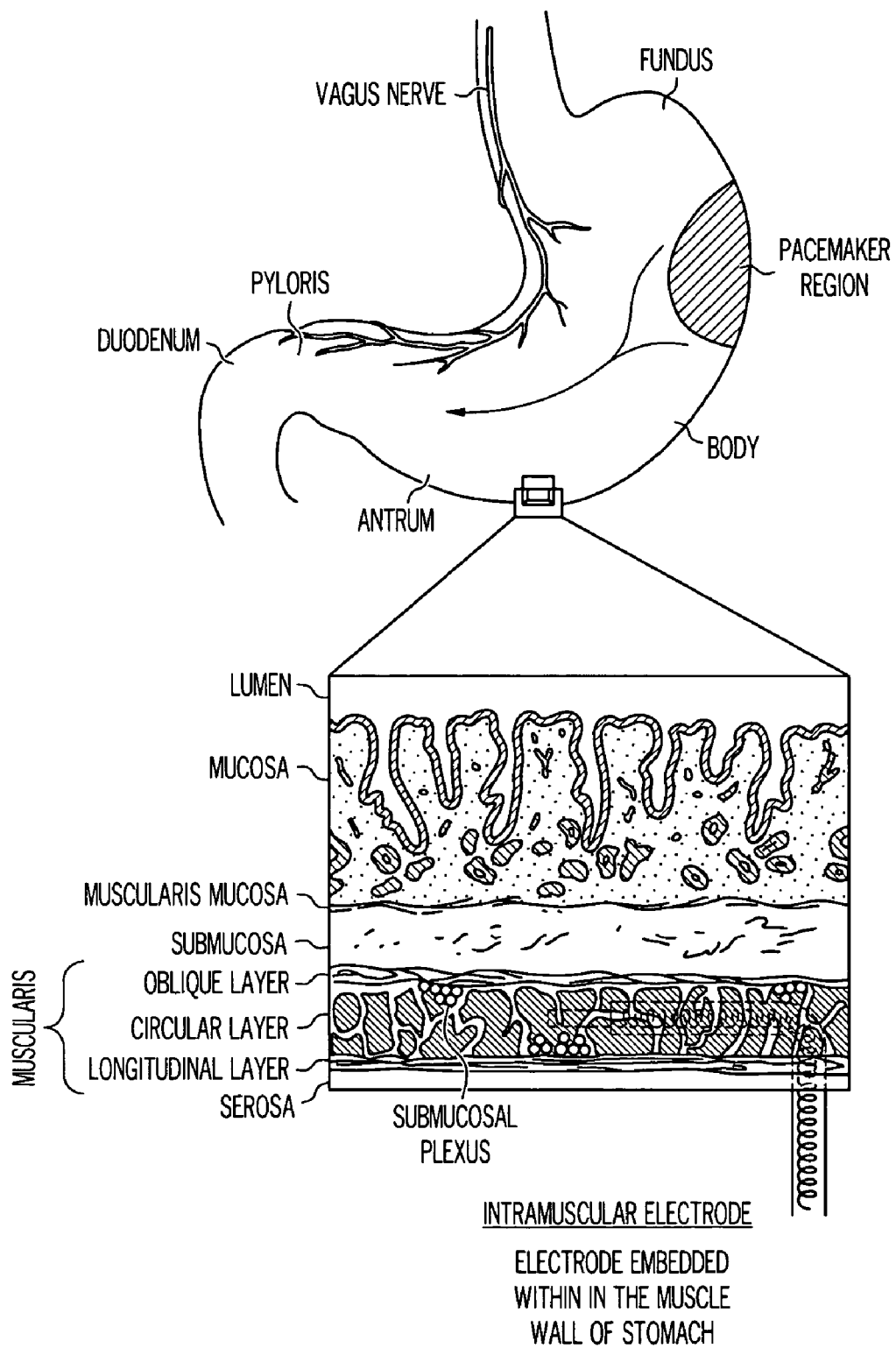
Figure 6F:
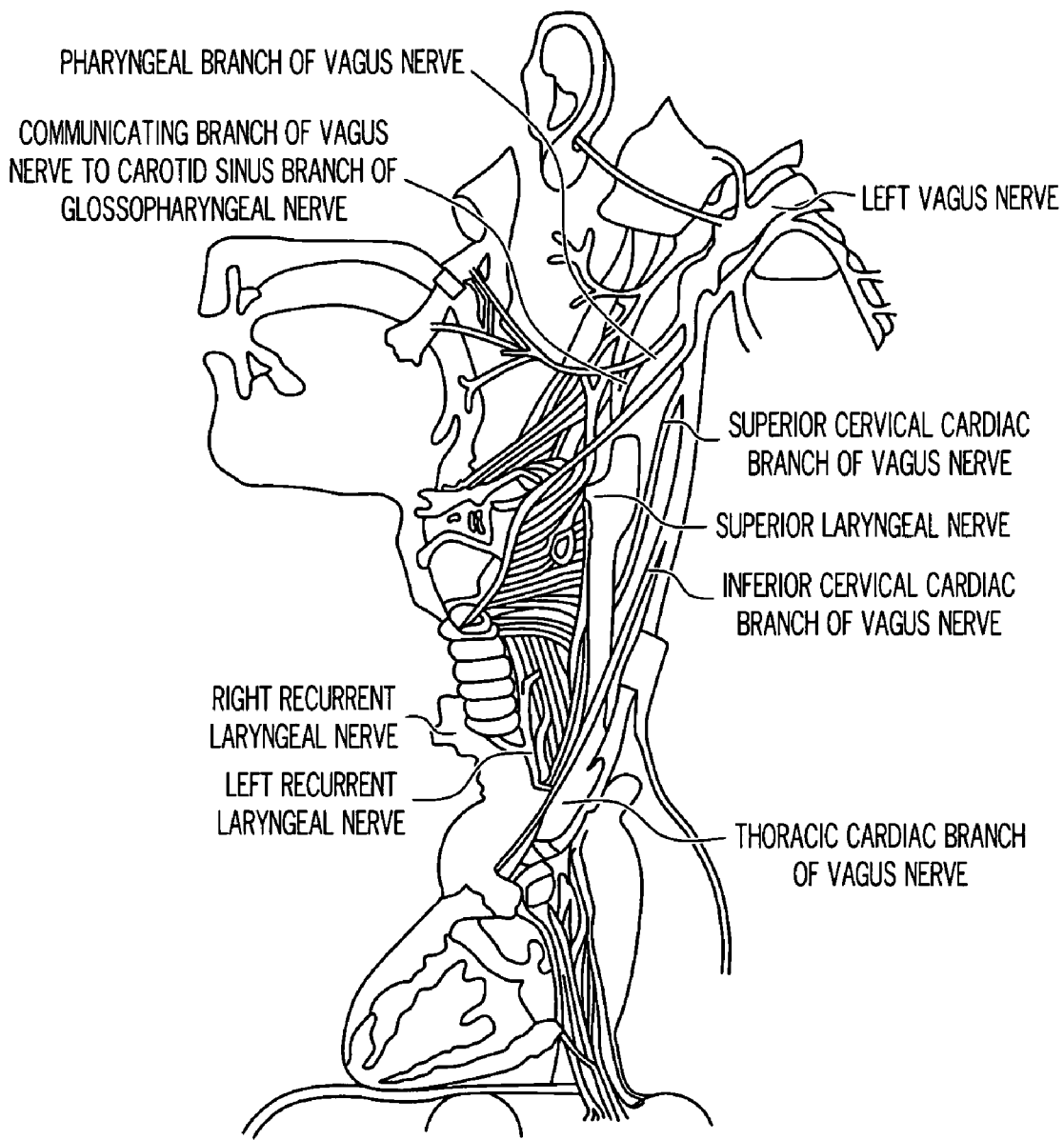

FIG. 4f shows lead 16 as a tri-polar cuff electrode, where cuff/anchor 19 is wrapped around desired nerve or nerve portion 8 to thereby secure the distal end of lead 16 to the nerve and position electrodes 20-22 against or near nerve or nerve portion 8. The Medtronic Model No. 3995 cuff electrode lead is one example of a lead that may be adapted for use in the present invention, the Instructions for Use manual of which entitled "INTERSTIM Manual: Model 3995 Implantable bipolar peripheral nerve and spinal root stimulation lead" is hereby incorporated by reference herein in its entirety.

FIGS. 5a through 5d illustrate representative cross-sectional views of gross and microscopic portions of a patient's stomach. The proximal stomach is the fundus and the distal stomach is the body and antrum. The pyloric sphincter joins the antrum and the duodenum. Parasympathetic input to the stomach is supplied by the vagus nerve and the sympathetic nervous system innervates the stomach through the splanchnic nerves. On the greater curvature of the stomach between the fundus and the body is the general region of the pacemaker of the stomach. A telescoped and cross-sectional view of the antrum is shown in the circle in the middle of FIG. 5a. This view shows the gastric wall with the mucosal layer and the muscularis. The outermost muscle layer is the longitudinal layer; and running perpendicular to the longitudinal muscle layer is the circular muscle layer. There is also an oblique muscle layer in the stomach. Between the circular muscle and longitudinal muscle layers are neurons of the myenteric plexus and the enteric nervous system. The second telescoped view shown in the lower circle illustrates the anatomic proximities of the myenteric neurons and the interstitial cells of Cajal in the myenteric region between the circular and longitudinal muscle layers. The processes of the interstitial cells interdigitate with circular muscle fibers and the myenteric neurons. The interstitial cells in the myenteric plexus area are thought to be responsible for generation of slow waves or pacesetter potentials. The interstitial cells are also found in the submucosal layers, the deep musculatures plexus, and the intramuscular layers of the stomach. Leads 16 and 18 and electrodes 20-24 may be implanted in or in the vicinity of any one or more of the serosa layer, the myenteric plexus, the submucosal plexus, or any of the various layers of the muscularis (i.e., the oblique, circular or longitudinal layers).

In accordance with several embodiments of the present invention, FIGS. 6a through 6f illustrate various locations for the placement of stimulation and sensing electrodes in and near the stomach. Electrodes 20 through 24 are placed in electrical contact or in proximity to target nerve or nerve portion 8. The electrode location is selected based upon the obtained innervation of the vagus nerve and digestive system, the selected location's suitability for electrode connection, and the degree to which the location proves efficacious for treating acid production or gastric acid pH in a particular patient. Locations most suitable for electrode attachment and connection should be easily accessible by surgical or endoscopic means, and further be sufficiently mechanically robust and substantial to secure and retain electrodes 20-24 of leads 16 and/or 18.

Some specific electrode locations that are well innervated, and surgically or endoscopically accessible include, but are not limited to: (a) the plexus on the anterior superior and/or the anterior inferior pancreaticoduodenal arteries; (b) the plexus on the inferior pancreaticoduodenal artery; (c) the plexus on the jejunal artery; (d) the superior mesenteric artery and plexus; (d) the plexus on the gastroepiploic arteries; (e) the celiac ganglia and plexus; (f) the splenic artery and plexus; (g) the left lesser thoracic splanchic nerve; (h) the left greater thoracic splanchic nerve; (i) the principal anterior gastric branch of the anterior vagal trunk; (j) the left gastric artery and plexus; (k) the celiac branch of the anterior vagal trunk; (l) the anterior vagal trunk; (m) proximal, distal or portions between the proximal and distal portions of the vagus nerve; (n) the hepatic branch of the anterior vagal trunk; (o) the right and/or left inferior phrenic arteries and plexus; (p) the anterior posterior layers of the lesser omenium; (q) the branch from the hepatic plexus to the cardia via the lesser omenium; (r) the right greater thoracic splanchic nerve; (s) the vagal branch from the hepatic plexus to the pylorus; (t) the right gastric artery and plexus. Note that as discussed above, it is contemplated in the present invention that multiple leads be employed.

Figure 7:
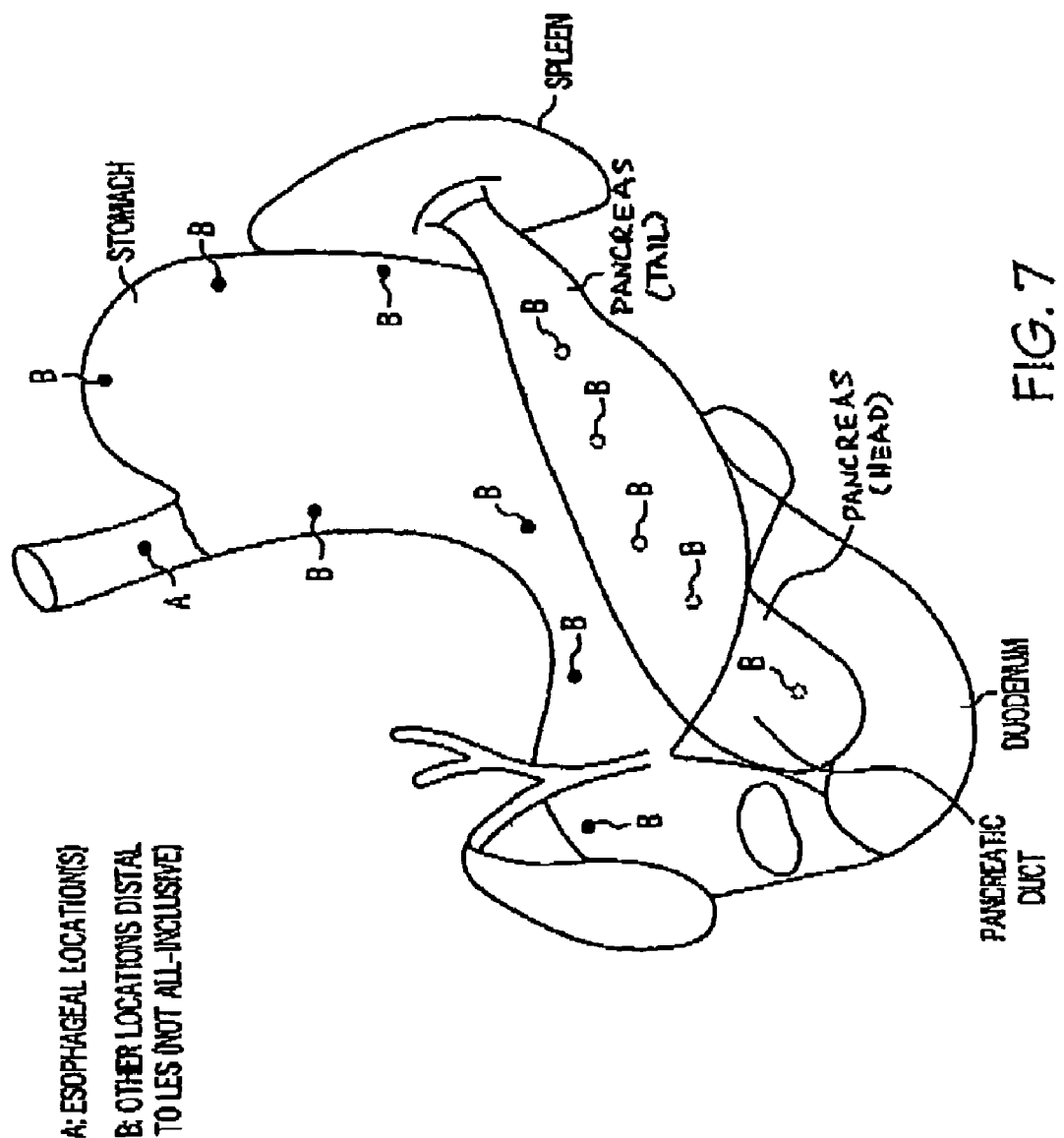
FIG. 7 illustrates various locations in or near the stomach and/or vagus nerve of a patient for feedback control sensors according to some embodiments of closed-loop feedback control systems of the present invention.

FIG. 7 illustrates some of the various locations in or near the stomach and/or vagus nerve of a patient for placing feedback control sensors according to some embodiments of closed-loop feedback control systems of the present invention.

Figure 8A:
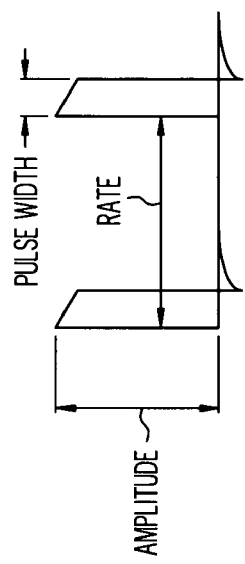
Figure 8B:
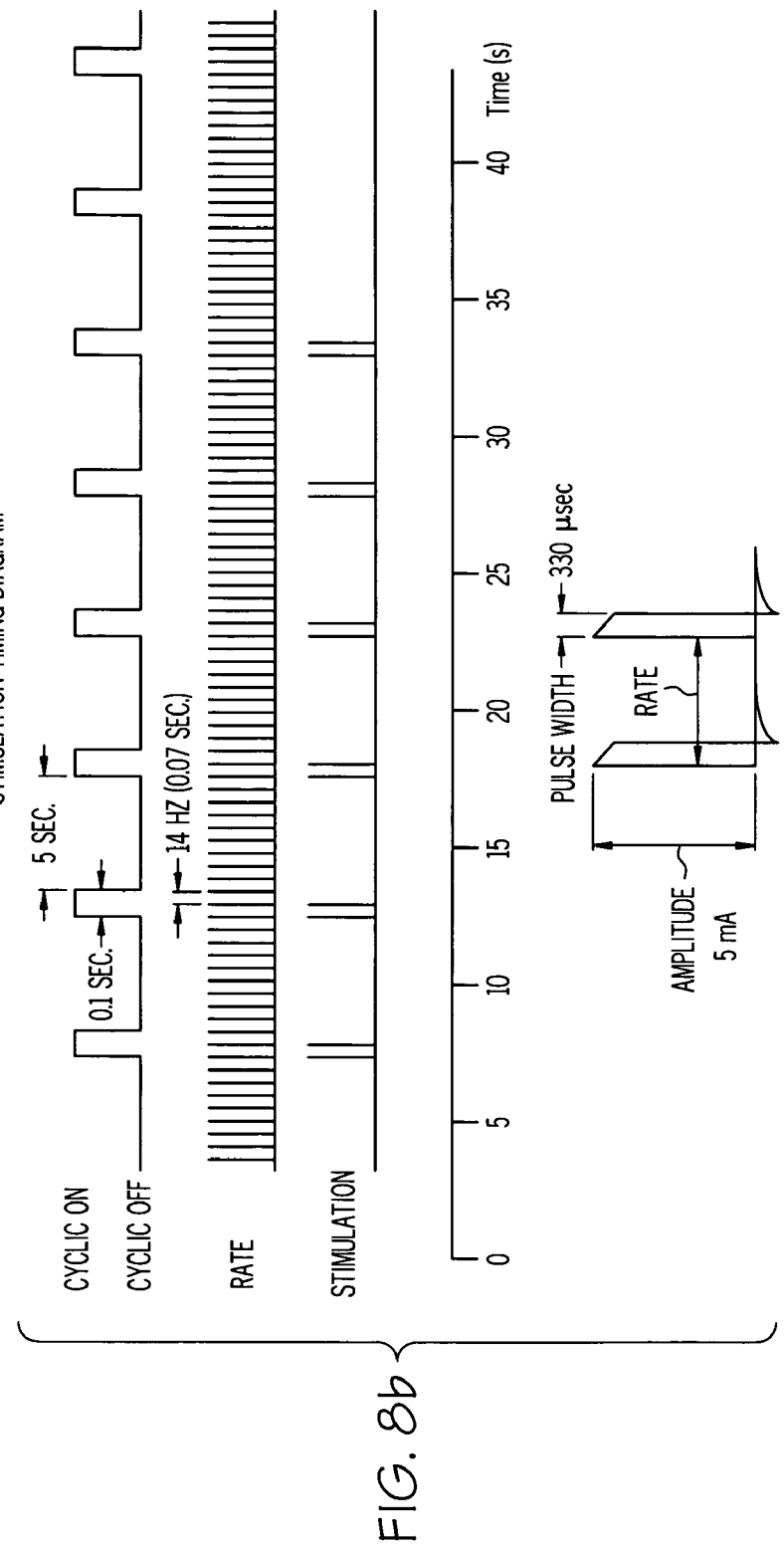

FIGS. 8a through 8d illustrate various representative electrical stimulation pulse, regime and control parameters according to some embodiments of the present invention. FIG. 8a illustrates a typical charge balanced square pulse used in many implantable electrical stimulation systems. As shown, amplitude, pulse width, and pulse rate are adjustable. FIG. 8b shows a timing diagram illustrating the output of INS 10 when the output signal provided thereby successively gated on and off. In FIG. 8b, INS 10 is set to a frequency of 14 pulses per second, but is gated on for 0.1 seconds, and off for 5 seconds, resulting in an output of two pulses every five seconds. The on and off gating periods may be adjusted over a wide range.

In the present invention, electrical stimulation signal parameters may be selected to influence gastric acid secretion through direct stimulation of a nerve or nerve portion 8, by stimulating afferent nerves or nerve portions 8, by stimulating efferent nerves or nerve portions 8, or by stimulating some combination of the foregoing nerves or nerve portions 8. The electrical stimulation signal is preferably charge-balanced for biocompatibility, and adapted to decrease gastric acid production and/or increase pH. For example, a gastric acid "decrease signal" is adapted to decrease the quantity of gastric acid secreted by the stomach lining, and accordingly has a frequency, phase, amplitude and morphology selected to signal the stomach to decrease the production of gastric acid. Such a "decrease signal" has a frequency ranging between about 0.10 pulses per minute and about 18,000 pulses per minute.

In the event multiple signals are employed to stimulate a desired site, the spatial and/or temporal phase between the signals may be adjusted or varied to produce the desired stimulation pattern or sequence. That is, in the present invention beam forming and specific site targeting via electrode array adjustments are contemplated. Examples of lead and electrode arrays and configurations that may be adapted for use in some embodiments of the present invention so as to better steer, control or target electrical stimulation signals provided thereby in respect of space and/or time include those disclosed in U.S. Pat. No. 5,501,703 to Holsheimer; U.S. Pat. No. 5,643,330 to Holsheimer; U.S. Pat. No. 5,800,465 to Thompson; U.S. Pat. No. 6,421,566 to Holsheimer; and U.S. Patent Application Publication No. 20020128694A1 to Holsheimer.

Representative ranges of preferred electrical pulse stimulation parameters capable of being delivered by INS 10 through leads 16 and 18 include the following:

| | |
|---|---|
| Frequency: | Between about 50 Hz and about 100 Hz; |
| | Between about 10 Hz and about 250 Hz; and |
| | Between about 0.5 Hz and about 500 Hz. |
| Amplitude: | Between about 1 Volt and about 10 Volts; |
| | Between about 0.5 Volts and about 20 Volts; and |
| | Between about 0.1 Volts and about 50 Volts. |
| Pulse Width: | Between about 180 microseconds and about 450 microseconds; |
| | Between about 100 microseconds and about 1000 microseconds; |

-continued

Between about 10 microseconds
and about 5000 microseconds.

Figure 9:
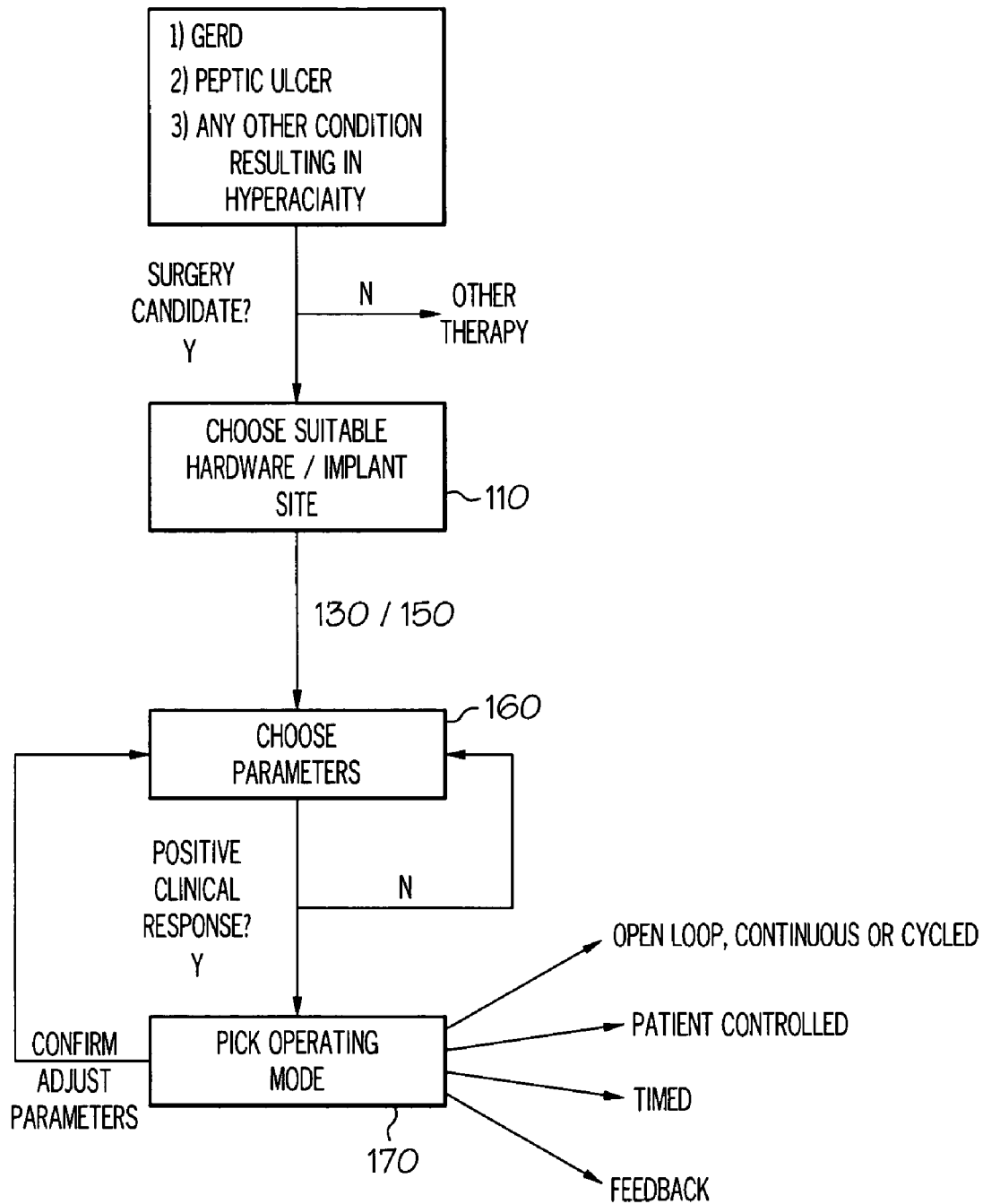
FIG. 9 illustrates several methods of stimulating a patient's stomach and/or vagus nerve so as to lower the amount of gastric acid secretions and/or to lower the acidity of such secretions in a patient.

Further exemplary stimulation parameters of the system of the present invention include:
(a) A stimulation signal frequency ranging between:
  (i) about 0.10 to about 18,000 pulses per minute;
  (ii) about 1 to about 5,000 pulses per minute;
  (iii) about 1 to about 1,000 pulses per minute;
  (iv) about 1 to about 100 pulses per minute;
  (v) about 3 to about 25 pulses per minute;
(b) A stimulation signal pulse width ranging between:
  (i) about 0.01 mS to about 500 mS;
  (ii) about 0.1 mS to about 100 mS;
  (iii) about 0.1 mS to about 10 mS;
  (iv) about 0.1 mS to about 1 mS;
(c) A stimulation signal current ranging between:
  (i) about 0.01 mA to about 500 mA;
  (ii) about 0.1 mA to about 100 mA;
  (iii) about 0.1 mA to about 10 mA;
  (iv) about 1 mA to 100 mA, and
  (v) about 1 to about 10 mA.
(d) A stimulation signal which occurs continuously in accordance with the parameters of (a), (b), and (c) above, or a combination thereof;
(e) A stimulation signal which occurs discontinuously when the system turns on and off, where on and off are defined as a cycle time which may vary between about 1 second and about 60 seconds (for example, on=0.1 seconds, and off=5 seconds; on=1.0 sec and off=4 seconds, and so on; see FIGS. 8c and 8d.
(f) Stimulation signals having morphologies best characterized as (i) spikes, (ii) sinusoidal waves, or (iii) square pulses;

FIG. 9 illustrates several methods of stimulating a patient's stomach and/or vagus nerve so as to lower the amount of gastric acid secretions and/or to lower the acidity of such secretions in a patient. In FIG. 9, step 110 is employed to determine one or more desired nerve stimulation locations (as illustrated in FIG. 5a through 5d and FIGS. 6a through 6f) positioned near or at one or more of the nerves 8, nerve portions 8, or locations near a nerve or nerve portion 8. Step 130 is employed to implant INS 10 in an appropriate location within the patient such that the proximal end of lead 16 may be operably connected thereto and such that INS 10 is placed in such a location that discomfort and the risk of infection to the patient are minimized. Next INS 10 is operably connected to lead 16, which may or may not require the use of optional lead extension 15 and lead connector 13. In Step 150, INS 10 is activated and stimulation pulses are delivered to electrodes 20, 21, . . . n through lead 16 to the desired nerve stimulation location. In step 160, the electrical pulse stimulation parameters are adjusted to optimize the therapy delivered to the patient. Such adjustment may entail one or more of adjusting the number or configuration of electrodes or leads used to stimulate the selected location, pulse amplitude, pulse frequency, pulse width, pulse morphology (e.g., square wave, triangle wave, sinusoid, biphasic pulse, tri-phasic pulse, etc.), times of day or night when pulses are delivered, pulse cycling times, the positioning of the lead or leads, and/or the enablement or disablement of "soft start" or ramp functions respecting the stimulation regime to be provided. In step 170 the operating mode of the implanted system is selected. Optionally, parameters selected in step 160 may be adjusted after the operating mode has been selected to optimize therapy.

Figure 10:
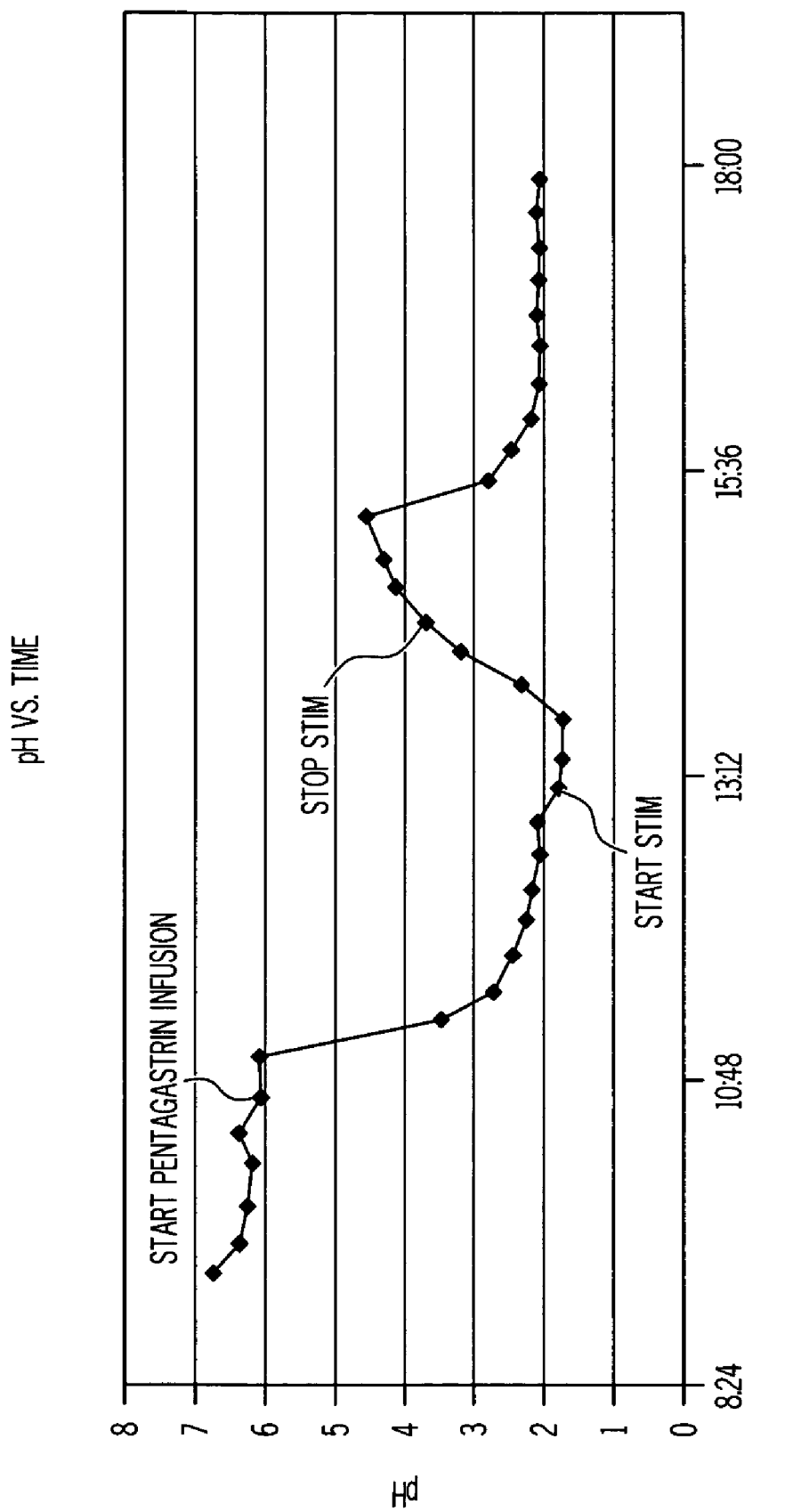
FIG. 10 shows test data obtained in accordance with one embodiment of the present invention.

FIG. 10 shows test data obtained in accordance with one embodiment of the present invention. Canines were instrumented acutely with four electrodes arranged circumferentially around the vagal neural plexus on the stomach. These leads were hooked up to an INS. The dog's stomachs were cannulated and clamped below the pylorus. Data collection occurred every 15 minutes. At the start of a 15-minute interval, 240 mL of warm saline was introduced into the stomach via the cannula. At the end of the interval, the saline was removed via suction and measured for volume and pH. During the course of the experiment, the dogs were infused continuously with pentagastrin to stimulate acid secretion. Various stimulation patterns-interspersed with rest periods were tried to modulate acid production.

The graph of pH versus time from the above-described animal experiment is shown in FIG. 10. These data suggest that vagal stimulation did have some effect on gastric acid secretions. When stimulation was applied, the pH rose and then fell when the INS was turned off.

In addition, in the present invention it is contemplated that drugs be delivered to specific sites within a patient using well known fully implantable drug pump devices in combination with providing electrical stimulation to the nerves or nerve portions described above. According to such a method, the drug pump may be incorporated into the same housing as INS 10, or be separate therefrom in its own hermetically sealed housing. The drug catheter attached to the implantable drug pump through which the drug is delivered to the specific site may also be incorporated into lead 16 or 18, or may be separate therefrom. Drugs or therapeutic agents delivered in accordance with this method include, but are not limited to, antibiotics, pain relief agents such as demerol and morphine, radioactive or radiotherapeutic substances or agents for killing or neutralizing cancer cells, genetic growth factors for encouraging the growth of healthy tissues, and the like.

Also hereby incorporated by reference herein in its entirety is U.S. Patent Application Number 20020082665A1 to Haller et al. published Jun. 27, 2002 and entitled "System and Method of Communicating between an Implantable Medical Device and a Remote Computer System or Health Care Provider." In the present invention it is further contemplated that the methods and devices described hereinabove be extended to include the communication system of Hailer et al. for at least one of monitoring the performance of INS 10 and/or an implantable drug pump implanted within the body of a patient, monitoring the health of the patient and remotely delivering an electrical stimulation and/or drug therapy to the patient through INS 10 and/or the optional implantable drug pump, INS 10 or the implantable drug pump being capable of bi-directional communication with a communication module located external to the patient's body, the system comprising: (a) INS 10 and optionally the implantable drug pump; (b) the communication module; (c) a mobile telephone or similar device operably connected to the communication module and capable of receiving information therefrom or relaying information thereto; (e) a remote computer system, and (f) a communication system capable of bidirectional communication.

According to further embodiments of the present invention, an ingestible or implantable pill-shaped or capsular device is employed which is capable of sensing one or more physical parameters such as pH, hormonal levels and the like, and recording, storing or transmitting to an external receiver by, for example, RF means, information regarding the parameter(s) sensed by the device acidity. The sensed parameter information may then be employed to control or refine the gastro-electric stimulation parameters. Examples of devices that may be so adapted in accordance with some embodiments of the present invention include:

U.S. Pat. No. 4,844,076 for "Ingestible Size Continuously Transmitting Temperature Monitoring Pill" to Lesho et al.;
U.S. Pat. No. 5,170,801 for "Medical Capsule Device Actuated by Radio-Frequency (RF) Signal" to Casper et al.;
U.S. Pat. No. 5,279,607 for "Telemetry Capsule and Process" to Schentag et al.;
U.S. Pat. No. 5,395,366 for "Sampling Capsule and Process" to D'Andrea et al.;
U.S. Pat. No. 6,285,897 for "Remote Physiological Monitoring System" to Kilcoyne et al.;
U.S. Pat. No. 6,428,469 for "Energy Management of a Video Capsule" to Iddan et al.;
U.S. Patent Application Publication No. 20020055734 for "Ingestible Device" to Houzego et al.;
U.S. Patent Application Publication No. 20020132226 for "Ingestible Electronic Capsule" to Nair et al.; and
U.S. Patent Application Publication No. 20020198470 for "Capsule and Method for Treating or Diagnosing the Intestinal Tract" to Imran et al..

According to other embodiments of the present invention, implantable sensors and/or stimulation modules or leads may be implanted in desired portions of the gastro-intestinal tract by means of a vacuum-operated device which is endoscopically or otherwise emplaced within the gastrointestinal tract, followed by a portion of the tract being sucked up into a receiving chamber of the device, and the sensor, module or lead being implanted within the tissue held within the receiving chamber. See, for example, U.S. Pat. No. 6,098,629 for "Submucosal Esophageal Bulking Device" to Johnson et al.; U.S. Pat. No. 6,338,345 for "Submucosal Prosthesis Delivery Device" to Johnson et al.; U.S. Pat. No. 6,401,718 for "Submucosal Prosthesis Delivery Device" to Johnson et al.; and PCT Patent Application WO 02087657 for "Gastric Device and Suction Assisted Method for Implanting a Device on a Stomach Wall" assigned to Intrapace, Inc.

In still further embodiments of the present invention, various components of the gastrointestinal electrical stimulation system may be extended, miniaturized, rendered wireless, powered, recharged or modularized into separate or discrete components in accordance with the teachings of, by way of example: U.S. Pat. No. 5,193,539 for "Implantable Microstimulator" to Schulman et al.; U.S. Pat. No. 5,193,540 for "Structure and Method of Manufacture of an Implantable Microstimulator" to Schulman et al.; U.S. Pat. No. 5,324,316 for "Implantable Microstimulators" to Schulman et al.; U.S. Pat. No. 5,358,514 for "Implantable Microdevice With Self-Attaching Electrodes" to Schulman et al.; U.S. Pat. No. 5,405,367 for "Structure and Method of Manufacture of an Implantable Microstimulator" to Schulman et al.; U.S. Pat. No. 5,957,958 for "Implantable Electrode Arrays" to Schulman et al.; U.S. Pat. No. 5,999,848 for "Daisy Chainable Sensors and Stimulators for Implantation in Living Tissue" to Gord et al.; U.S. Pat. No. 6,051,017 for "Implantable Microstimulator and Systems Employing the Same" to Loeb et al.; U.S. Pat. No. 6,067,474 for "Implantable Device With Improved Battery Recharging and Powering Configuration" to Schulman et al.; U.S. Pat. No. 6,205,361 for "Implantable Expandable Multicontact Electrodes" to Kuzma et al.; U.S. Pat. No. 6,212,431 for "Power Transfer Circuit for Implanted Devices" to Hahn et al.; U.S. Pat. No. 6,214,032 for "System for Implanting a Microstimulator" to Loeb; U.S. Pat. No. 6,315,721 for "System of Implantable Devices for Monitoring and/or Affecting Body Parameters" to Schulman et al.; U.S. Pat. No. 6,393,325 for "Directional Programming for Implantable Electrode Arrays" to Mann et al.; U.S. Pat. No. 6,516,227 for "Rechargeable Spinal Cord Stimulator System" to Meadows et al.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of any particular specific configuration of an INS, leads or electrodes shown explicitly in the drawings hereof. Those skilled in the art will understand immediately that many variations and permutations of known implantable devices may be employed successfully in the present invention.

In the claims, means plus function clauses are intended to cover the structures described herein as performing the recited function and their equivalents. Means plus function clauses in the claims are not intended to be limited to structural equivalents only, but are also intended to include structures which function equivalently in the environment of the claimed combination. All printed publications and patents referenced hereinabove are hereby incorporated by referenced herein, each in its respective entirety.

We claim:

1. A method comprising:
   generating electrical stimulation having one or more parameters selected to reduce acidity of gastric acid secretions in a patient; and
   delivering the electrical stimulation to one or more portions of a gastrointestinal tract of the patient via an implantable electrical lead to reduce the acidity of the gastric acid secretions in the patient.

2. The method of claim 1, wherein the implantable electrical lead is selected from the group consisting of an intramuscular lead, a unipolar lead, a bipolar lead, a tri-polar lead, a quadrapolar lead, and a multi-polar lead.

3. The method of claim 1, wherein the implantable electrical lead is selected from the group consisting of a beam steering lead comprising multiple electrodes and a lead comprising multiple electrodes disposed in an areal pattern on a planar or curved surface.

4. The method of claim 1, wherein the implantable electrical lead is selected from the group consisting of a cuff lead, a paddle lead, a tined lead, and a lead having an active fixation device.

5. The method of claim 1, wherein the implantable electrical lead includes a fixation device selected from the group consisting of a suture sleeve, a barb, a helical screw, a hook and a tissue in-growth mechanism.

6. The method of claim 1, wherein the implantable electrical lead further comprises one or more electrodes configured to operate in conjunction with an electrically conductive portion of an implantable pulse generator acting as an indifferent electrode.

7. The method of claim 1, wherein the implantable electrical lead is a first implantable electrical lead, the method further comprising providing, implanting, operably connecting and delivering electrical stimuli from a second implantable medical electrical lead configured for implantation adjacent, around or in at least one of the stomach, the vagus nerve, the plexus on the anterior superior and/or the anterior inferior pancreaticoduodenal arteries, the plexus on the inferior pancreaticoduodenal artery, the plexus on the jejunal artery, the superior mesenteric artery and plexus, the plexus on the gastroepiploic arteries, the celiac ganglia and plexus, the splenic artery and plexus, the left lesser thoracic splanchic nerve, the left greater thoracic splanchic nerve, the principal anterior gastric branch of the anterior vagal trunk, the left gastric artery and plexus, the celiac branch of the anterior vagal trunk, the anterior vagal trunk, proximal, distal or portions between the proximal and distal portions of the vagus nerve, the hepatic branch of the anterior vagal trunk, the right and/or left inferior phrenic arteries and plexus, the anterior posterior layers of the lesser omenium, the branch from the hepatic plexus to the cardia via the lesser omentum, the right greater thoracic splanchnic nerve, the vagal branch from the hepatic plexus to the pylorus, the right gastric artery, the plexus, and the intestine, or branches or portions thereof, wherein the second lead comprises proximal and distal ends and at least one electrode.

8. The method of claim 7, further comprising delivering the electrical stimulation through tissue disposed between the electrodes located on the first and second leads.

9. The method of claim 1, further comprising providing a lead extension, operably connecting the lead extension between a proximal end of the implantable electrical lead and an implantable pulse generator, and delivering the electrical stimulation pulses through the lead extension and the implantable electrical lead.

10. The method of claim 1, wherein the implantable electrical lead is selected from the group consisting of a lead comprising a lead body less than about 5 mm in diameter, and a lead comprising a lead body less than about 1.5 mm in diameter.

11. The method of claim 1, wherein the implantable electrical lead has at least two electrodes, wherein an inter-electrode distance of the implantable electrical lead is selected from the group consisting of about 1 mm, about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, and about 30 mm.

12. The method of claim 1, wherein the implantable electrical lead has at least one electrode, wherein the at least one electrode of the implantable electrical lead has an electrode surface area ranging between about 1.0 sq. mm and about 100 sq. mm, between about 2.0 sq. mm and about 50 sq. mm, or between about 4.0 sq. mm and about 25 sq. mm.

13. The method of claim 1, wherein the implantable electrical lead includes at least a proximal end and a distal end, wherein the distance between the proximal and distal ends of the implantable electrical lead is selected from the group consisting of less than about 4 inches, about 4 inches, about 6 inches, about 8 inches, about 10 inches, about 12 inches, about 14 inches, about 16 inches, about 18 inches, and about 20 inches.

14. The method of claim 1, wherein generating electrical stimulation comprises generating electrical stimulation pulses via an implantable pulse generator, and wherein the implantable pulse generator comprises an electronic circuitry architecture selected from the group consisting of a microprocessor-based architecture, a logic architecture and a state machine architecture.

15. The method of claim 1, wherein generating electrical stimulation comprises generating electrical stimulation pulses via an implantable pulse generator, the method further comprising providing an external programming unit and effecting telemetric communication between the programming unit and the implantable pulse generator.

16. The method of claim 1, wherein generating electrical stimulation comprises generating electrical stimulation pulses via an implantable pulse generator, and wherein the implantable pulse generator further comprises at least one of a primary battery power source and a secondary battery power source.

17. The method of claim 1, wherein generating electrical stimulation comprises generating electrical stimulation pulses via an implantable pulse generator, and wherein the implantable pulse generator is configurable so as to permit at least one of the frequency, rate, amplitude, phase, width and morphology of the pulses generated and delivered thereby to be varied programmably by a user.

18. The method of claim 1, wherein the implantable electrical lead is configured for percutaneous introduction and implantation within the patient and the implantable electrical lead is electrically coupled to a pulse generator outside of the patient configured for generating electrical stimulation.

19. The method of claim 1, wherein generating electrical stimulation comprises generating electrical stimulation pulses via an implantable pulse generator, and wherein the implantable pulse generator and the implantable electrical lead are capable of generating and delivering electrical pulses having frequencies ranging between about 50 Hz and about 100 Hz, between about 10 Hz and about 250 Hz, and between about 0.5 Hz and about 20,000 Hz.

20. The method of claim 1, wherein generating electrical stimulation comprises generating electrical stimulation pulses via an implantable pulse generator, and wherein the implantable pulse generator and the implantable electrical lead are capable of generating and delivering electrical pulses having amplitudes ranging between about 1 Volt and about 10 Volts, between about 0.5 Volts and about 20 Volts, and between about 0.1 Volts and about 50 Volts.

21. The method of claim 1, wherein generating electrical stimulation comprises generating electrical stimulation pulses via an implantable pulse generator, wherein the implantable pulse generator and the implantable electrical lead are capable of generating and delivering electrical pulses having pulse widths ranging between about 180 microseconds and about 450 microseconds, between about 100 microseconds and about 1000 microseconds, and between about 10 microseconds and about 5000 microseconds.

22. The method of claim 1, wherein generating electrical stimulation comprises generating electrical stimulation pulses via an implant able pulse generator, and wherein the implantable pulse generator and the implantable electrical lead and at least a second lead are capable of generating and delivering electrical pulses having varying spatial or temporal phases.

23. The method of claim 1, further comprising delivering a drug to the patient.

24. The method of claim 23, further comprising providing, implanting and activating an implantable drug pump for providing the drug to the patient.

25. The method of claim 1, further comprising providing at least one sensor to sense a physical condition, and adjusting the stimulation based on the sensed condition.

26. The method of claim 1, wherein the implantable electrical lead has a lead body selected from the group consisting of polyurethane and silicone.

27. The method of claim 1, wherein the implantable electrical lead comprises electrical conductors disposed within the body thereof and extending between the proximal and distal ends of the lead wherein the conductors are formed of coiled, braided or stranded wires.

28. The method of claim 1, wherein the implantable electrical lead comprises at least one of at least one ring electrode, at least one coiled electrode, at least one button electrode, at least one electrode formed from a portion of wire, a barb or a hook, a spherically-shaped electrode, or a helically-shaped electrode.

29. The method of claim 1, wherein generating electrical stimulation comprises generating electrical stimulation having one or more parameters selected to reduce acidity of gastric acid secretions in a patient and reduce an amount of the gastric acid secretions in the patient, and delivering the electrical stimulation comprises delivering the electrical stimulation to one of more portions of a gastrointestinal tract of the patient via an implantable electrical lead to reduce the acidity of the gastric acid secretions in the patient and reduce the amount of the gastric acid secretions in the patient.

30. The method of claim 1, wherein delivering the electrical stimulation to one or more portions of a gastrointestinal tract of the patient via an implantable electrical lead to reduce the acidity of the gastric acid secretions in the patient comprises delivering the electrical stimulation to one of the stomach, the plexus on the anterior superior and/or the anterior inferior pancreaticoduodenal arteries, the plexus on the inferior pancreaticoduodenal artery, the plexus on the jejunal artery, the superior mesenteric artery and plexus, the plexus on the gastroepiploic arteries, the celiac ganglia and plexus, the splenic artery and plexus, the left lesser thoracic splanchic nerve, the left greater thoracic splanchic nerve, the principal anterior gastric branch of the anterior vagal trunk, the left gastric artery and plexus, the celiac branch of the anterior vagal trunk, the anterior vagal trunk, proximal, distal or portions between the proximal and distal portions of the vagus nerve, the hepatic branch of the anterior vagal trunk, the right and/or left inferior phrenic arteries and plexus, the anterior posterior layers of the lesser omenium, the branch from the hepatic plexus to the cardia via the lesser omentum, the right greater thoracic splanchic nerve, the vagal branch from the hepatic plexus to the pylorus, the right gastric artery, the plexus, and the intestine, or branches or portions thereof wherein a second lead comprises proximal and distal ends and at least one electrode.

31. The method of claim 1, wherein delivering the electrical stimulation to one or more portions of a gastrointestinal tract of the patient via an implantable electrical lead to reduce the acidity of the gastric acid secretions in the patient comprises delivering the electrical stimulation to one of a stomach and an intestine of the patient.

32. The method of claim 1, wherein generating electrical stimulation comprises generating electrical stimulation via an implantable stimulation generator implanted within the patient and coupled to the implantable electrical lead.

33. The method of claim 32, further comprising modifying one or more parameters of the stimulation via a programming unit in telemetric communication with the implantable stimulation generator.

* * * * *

UNITED STATES PATENT AND TRADEMARK OFFICE
CERTIFICATE OF CORRECTION

PATENT NO. : 7,620,454 B2
APPLICATION NO. : 10/441785
DATED : November 17, 2009
INVENTOR(S) : Dinsmoor et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 192 days.

Signed and Sealed this

Twenty-sixth Day of October, 2010

David J. Kappos
*Director of the United States Patent and Trademark Office*